United States Patent [19]
Noritake et al.

[11] Patent Number: 6,014,888
[45] Date of Patent: Jan. 18, 2000

[54] WORKING ENVIRONMENT DENSITY MEASURING METHOD

[75] Inventors: Yuji Noritake, Kanagawa; Hisako Murobushi, Tokyo; Hajime Hori, Kitakyushu, all of Japan

[73] Assignee: Ricoh Company, Ltd., Tokyo, Japan

[21] Appl. No.: 09/157,097

[22] Filed: Sep. 18, 1998

Related U.S. Application Data

[62] Division of application No. 08/748,980, Nov. 14, 1996, Pat. No. 5,861,053.

[30] Foreign Application Priority Data

Nov. 14, 1995 [JP] Japan .................................... 7-295862
Nov. 6, 1996 [JP] Japan .................................... 8-294195

[51] Int. Cl.$^7$ .............................. G01N 30/02; G01N 9/00
[52] U.S. Cl. ....................... 73/23.35; 73/23.41; 73/30.01
[58] Field of Search ............................. 73/23.2, 23.22, 73/23.28, 24.05, 30.01, 23.42, 30.04, 23.36, 23.35, 23.41, 23.4

[56] References Cited

U.S. PATENT DOCUMENTS

| | | | |
|---|---|---|---|
| 3,295,359 | 1/1967 | Peck . | |
| 3,638,396 | 2/1972 | Lovelock | 73/23.35 |
| 3,638,397 | 2/1972 | Charlton | 73/23.41 |
| 4,178,794 | 12/1979 | Jugle et al. | 73/863.21 |
| 4,277,259 | 7/1981 | Rounbehler et al. | 73/863.21 |
| 4,375,667 | 3/1983 | Buchan | 73/863.23 |
| 4,389,903 | 6/1983 | Bertone et al. | 73/863.23 |
| 4,425,810 | 1/1984 | Simon et al. | 73/23.35 |
| 4,721,517 | 1/1988 | Cloutier | 73/863.23 |
| 4,961,916 | 10/1990 | Lesage et al. | 73/863.21 |
| 5,205,155 | 4/1993 | Cooper | 73/28.04 |
| 5,465,607 | 11/1995 | Corrigan et al. | 73/23.36 |
| 5,526,675 | 6/1996 | Ratton | 73/23.2 |
| 5,553,507 | 9/1996 | Basch et al. | 73/863.01 |
| 5,702,506 | 12/1997 | Shih et al. | 73/31.02 |

*Primary Examiner*—Hezron Williams
*Assistant Examiner*—Helen C. Kwok
*Attorney, Agent, or Firm*—Oblon, Spivak, McClelland, Maier & Neustadt, P.C.

[57] ABSTRACT

An environmental air is sucked by the pump with control unit, and organic solvent contained in the environmental air is collected by the absorbent. Organic solvent having passed through the absorbent is detected by the semiconductor gas sensor. If passage of a material to be measured is detected by the semiconductor gas sensor, operation of the pump with control unit is stopped, and the operation for collecting the material is terminated. Then the absorbent is taken out from the collecting tube, the material collected is quantified by means of gas chromatography, and the density is measured. With this configuration, measurement of a density of a material to be measured in a working environment can be executed accurately.

2 Claims, 22 Drawing Sheets

WORKING ENVIRONMENT DENSITY MEASURING METHOD

This application is a Division of application Ser. No. 08/748,980 filed on Nov. 14, 1996, now U.S. Pat. No. 5,861,053.

FIELD OF THE INVENTION

The present invention relates to a solid material collector for collecting a material to be measured by absorbing thereto the material as well as to a density measuring method for measuring the density thereof, and further to a gas mask as well as to an air line mask each for improving safety thereof by detecting any of poisonous substances which has passed the solid material collector.

BACKGROUND OF THE INVENTION

As a method of measuring a density of poisonous material such as organic solvent vapor in a working environment and a dose of a substance to which a person is exposed in the working environment, there has been known a method using an absorbent such as activated carbon, so-called a solid material collecting method. Generally, following effects can be obtained with this solid material collecting method.
(1) Substantially 100% of organic solvent vapor or the like can be collected with an absorbent.
(2) Time-weighted mean of density can be obtained. However with the direct collecting method, it is possible to measure only a transitional density.
(3) As organic solvent vapor or the like can be condensed, it is possible to quantify the vapor or the like in a low density. And for this reason, a range in which the vapor or the like can be measured is very wide.
(4) A method of gas chromatography (described as "GC" hereinafter) is used for quantifying the vapor or the like, so that even mixed gas or mixed vapor can be measured.

However, an absorbent used for the solid material collecting method has a limited capacity for absorbing a solid material. For this reason, when the collection is executed for a long period of time, poisonous substances pass through the absorbent. If any poisonous substances pass therethrough, the measurement will become incorrect.

For this reason, many of commercial solid material collectors have such configuration that adsorbents are packed therein in two layers, in an upstream side as well as in a downstream side of the device. The absorbent in the upstream side thereof is used as a sample to be analyzed by means of the GC. The absorbent in the downstream side thereof is used for checking whether any of the substances has passed through the absorbent or not.

With this configuration, the material to be measured passing through the absorbent in the upstream side is collected by the absorbent positioned in the downstream side. Accordingly, if any material to be measured is detected in the absorbent in the downstream side by analyzing it, the fact indicates that the material passed through the absorbent in the upstream side. So, effectiveness of the measurement is determined according to a quantity of the material having passed through the absorbent in the upstream side. If the quantity is too large, a result of the measurement is not reliable, which indicates that the measurement is a waste of time.

FIG. 24 shows a partially broken perspective view of a solid material collector 900 based on the conventional technology. An absorbent 903 in the downstream side and that 902 in the upstream side thereof are serially packed in a collecting tube 901. Activated carbon is used for the absorbents 902 and 903. A duct 904 comes out from an edge section of the collecting tube 901. A small size electric pump 905 is connected to the edge section of this duct 904. The reference numeral 906 indicates a clip for attaching this device to a user. When the pump 905 is driven, environmental air is introduced into the collecting tube 901 through an opening edge thereof. Organic solvent contained in the environmental air is collected by the absorbent 902. The air passing through the adsorbents 902 and 903 passes through the duct 904 to be discharged from an air outlet port of the pump 905.

FIG. 25 is an explanatory view showing how an operator wears the solid material collector 900. The collecting tube 901 is attached with a clip 906 onto a shoulder portion of the clothes which a user M wears. The pump 905 is fixed to a belt or the similar position of the user M. The user M works with this solid material collector 900 on. When the work is finished, the absorbent 902 in the upstream side as well as that 903 in the downstream side are taken out from the collector. Then, the absorbent 902 in the upstream side is analyzed with the GC to quantify the collected material to be measured. The absorbent 903 in the downstream side is also analyzed. If any material to be measured is detected from the absorbent 903 in the downstream side, it is understood that the material passed through the absorbent 902 in the upstream side. When a quantity of the detected material to be measured is larger than a specified quantity, a density of the material in the environment or a dose of the material to which a person is exposed can not accurately be measured. Accordingly, it can be determined that this measurement is invalid.

However, in the solid material collector 900 described above, effectiveness of the measurement can not be determined before the collecting work is finished. For this reason, the measurement can not always accurately be made. And also, the absorbent 902 is sometimes wasted thereby.

There has also been known a method in which a period of time from the beginning of the measurement until the absorbent 902 is about to be passed through by the material to be measured under a constant gas density is previously measured and the measurement is stopped just before passage of the previously determined period of time. However, a gas density in the working environment generally changes from time to time and from place to place. Also a user tends to move around in the working environment. And for this reason, the user can not accurately estimate the period of time until a material to be measured starts passing through the absorbent in the upstream side.

It is also conceivable to make a capacity of an absorbent larger. However, when the capacity is made larger, a capacity of a pump is required to be made larger proportionately. For this reason, a size of the pump becomes large, which lowers portability of the solid material collector.

By the way, the absorbent described above is also used for a gas mask or an air line mask used in cases of spraying agricultural chemicals, handling drugs, painting, or cleaning or the like, which is different from the purpose of the absorbent when used for measuring a density of poisonous materials in a working environment or a dose of the substances to which a person is exposed. In these cases, the passage of the poisonous material through the absorbent becomes an extremely serious matter. If the determination that the passage of a poisonous material through the absorbent has been generated is made after it actually occurred, sometimes it is too late.

Currently, there has been employed a method in which a period of working time (a period of time before passage of a poisonous material through an absorbent occurs) is computed from a gas density in the working environment and the work is stopped before the passage actually occurs. However, there is the fear that the period of working time is reduced because the gas density in the working environment is not uniform. Especially, in a case where fatally poisonous materials such as chemical weapons or the like are handled, it may bring about a serious danger to an operator.

SUMMARY OF THE INVENTION

It is a first object of the present invention to provide a solid material collector which is small in size and can efficiently and accurately measure a density of of a poisonous material in a working environment or a dose of a material to be measured to which a person is exposed, as well as to provide a density measuring method.

Further, it is a second object of the present invention to provide a high safety gas mask as well as a high safety air line mask.

To achieve the object described above, a solid material collector according to the present invention detects passage of a material to be measured in a collecting process by a detecting means. With a collecting means having a double-layer structure based on the conventional technology, a result of measurement is unreliable in many cases. However, the solid material collector can detect the passage of a material to be measured through an absorbent in the collecting step at real time, which makes it possible to stop the operation for collecting poisonous materials immediately when the passage is detected. Therefore a result of measurement is reliable. Also, it is possible to perform measurement even after the passage is generated, so that a result of measurement is quite accurate. In recent years, many detecting means such as a gas sensor and the like have been developed, and use of the means for solving the problems relating to the passage described above is very effective. The detecting means such as a gas sensor is extremely small in size, which makes it possible to reduce size of a collector.

A solid material collector according to the present invention detects the passage before it actually occurs. By providing the detecting means at a position adjacent to an edge in the downstream side of the collecting means, a material to be measured can be detected right before the passage is actually generated. Thus, measurement can be executed more accurately.

A solid material collector according to the present invention may comprise various types of collecting means, however only especially useful ones are described herein (activated carbon, silica gel, porous polymer heads, Florisil (a magnesium silicate absorbent), or material to be measured impregnated therein). For instance, activated carbon has the advantage that there is no need to cool it down for eliminating water content in air and improving the collecting efficiency. When a density of a material to be collected in the collecting means reaches its saturation, a material with lower adhesiveness to an absorbent starts passing through the absorbent. On the other hand, if a gas sensor is used as the detecting means, it detects the material to be measured non-selectively regardless of its type. The object material for measurement which first passes through activated carbon is detected by the detecting means. Thus, by stopping an operation for collecting the materials at a point of time when any material first passes through the collecting means, passage of other materials each as an object for measurement can be prevented. As a result, a result of measurement can be prevented from becoming unreliable. Also, measurement can be executed quite accurately.

A solid material collector according to the present invention of the present invention uses a semiconductor gas sensor as the detecting means. The semiconductor gas sensor is extremely effective for detecting organic solvent vapor. It can detect almost all types of organic solvent vapor non-selectively, and it has high sensitivity. Also, it is low in price. Therefore, it is very useful as the detecting means for detecting the passage of a material to be collected through the collecting means.

The solid material collector according to the present invention asks a user to take any appropriate procedure, because a result of measurement will become unreliable if the solid material collector continues an operation for collecting the material to be measured even after the passage has occurred. The appropriate procedure includes stopping the operation for collecting the material. An alarming means includes sound, color, light, vibration or the like. As a result, measurement can be executed quite accurately and the result is very reliable.

A solid material collector according to the present invention stops operations of a sucking means and stops an operation for collecting a material to be measured when a quantity of materials having passed through the collecting means has exceeded a specified value. With this configuration, effects of the passage will be suppressed to a minimum level, and measurement can be executed accurately. Also, a result of measurement is prevented from becoming unreliable. It should be noted that the specified value described above is set according to sensitivity of the detecting means. For example, it is set according to a result of an experiment for studying a relation between a result of detection for the passage by the detecting means and actual state of the passage, or the like. Details on this matter will be discussed in the section for detailed description of the preferred embodiments of the present invention.

In the solid material collector according to the present invention, sensitivity of the detecting means varies according to a material to be measured. Thus, the specified value can be changed freely according to the material to be measured. Therefore, measurement can be executed accurately.

The solid material collector according to the present invention records a point of time when operation of the sucking means is started, and measures an actual period of time when collecting is actually executed. And it quantifies the material to be measured from a flow rate of environmental air during the period of time. With this configuration, it is possible to exclude a period of time when the passage occurred from an actual period of time for measurement, so that measurement can be executed accurately. In addition, as a start/stop time recording means, a timer device, which is commercially available, can be used. Therefore, the solid material collector can be provided at low cost.

In the solid material collector according to the present invention, a plurality of the detecting means are provided, and if dispersion is generated in output from one detecting means, another detecting means is selected. With this configuration, reliability of output from the detecting means becomes higher, and measurement can be executed accurately. In a case where dispersion is generated in all the detecting means, it is necessary to replace all the detecting means with new ones.

In a density measuring method according to the present invention, the operation for collecting the material to be measured is stopped stops when passage occurs, and measures density is measured in a state where there is no effect of the passage. Thus, measurement can be executed accurately. Also a result of measurement is reliable. The solid material collector described above detects the passage in a step of collecting, so that it is suitable for carrying out the density measuring method.

In a density measuring method according to the present invention, the passage is detected is detected right before it is actually generated, so that the operation for measurement can be executed in a state where no passage is generated. To detect the passage right before it is actually generated, the material to be measured is detected at a position adjacent to an edge section in the downstream side of the collecting means. With this configuration, measurement can be executed more accurately.

A gas mask according to the present invention incorporates a detecting means at a position adjacent to an edge in the downstream side of the collecting means. With this configuration, the passage can be detected right before it is generated. Therefore, the user can take required measures when the passage is detected. The specified measures include closing a shutter so that poisonous gas will not come into a mask body and breathing air from an oxygen cylinder, evacuating a working site immediately for changing the collecting means to a new one. As a result, higher safety of the gas mask is insured.

A gas mask according to the present invention detects poisonous substance having passed through the collecting means in the upstream side and collects the poisonous substance with the collecting means in the downstream side. The user can take necessary measures when the passage is detected. The user will not receive any damage with the poisonous substance having passed through the collecting means in the upstream side. This insures higher safety of the gas mask. As the user will stop using the gas mask when the poisonous substance is detected, capacity of the collecting means in the downstream side may be smaller than that of the collecting means in the upstream side. Therefore, the gas mask can be provided at low cost.

A gas mask according to the present invention detects passage of the poisonous substance with a detecting means. This configuration is simpler than that of the gas mask described above, which makes its cost less expensive. The gas mask with this configuration detects the poisonous substance which passed through the collecting means previously, so that it is suitable for dealing with substance which is comparatively less harmful to a human body. But it is not suited to use for detecting fatally poisonous substances such as chemical weapons.

In a gas mask according to the present invention, various types of collecting means can be used. For instance, activated carbon is excellent for collecting organic solvent. Silica gel is effective for collecting polarized gaseous materials. Porous polymer beads is suitable for collecting instable compounds. Florisil is suitable for collecting chlorinated biphenyl (PCB). As for filter paper with a reagent impregnated therein, filter paper with 2-pyridyl piperazine impregnated therein is used for measuring toluene-diisocyanate (TDI); and filter paper with triethanolamine impregnated therein is used for measuring nitrogen oxide or the like.

A gas mask according to the present invention comprises a semiconductor gas sensor, which is extremely effective for detecting organic solvent vapor. The reason is that the semiconductor gas sensor can detect almost all types of organic solvent vapor non-selectively. Therefore, it can detect passage of the poisonous substance without fail. Thus, higher safety of the gas mask is insured.

A gas mask according to the present invention notifies a user for the necessity to take an appropriate measure for the purpose to prevent the gas mask from being used in a state where any poisonous substance has passed through the collecting means. The appropriate measures include immediate evacuation from the working site. An alarming means includes sound, color, light, vibration or the like. As a result, higher safety of the gas mask is insured.

In the gas mask according to the present invention, a plurality of the detecting means are provided, and if dispersion is generated in output from one detecting means, the detecting means is switched to another one. As a result, higher reliability of the output from the detecting means is provided, and also higher safety of the gas mask is insured.

In a gas mask according to the present invention, when the passage is detected, the fact is notified to a manager or a person other than the user. Notification is made by radio or the like. Because of the notification, the person other than the user can realize that the user is in a dangerous situation. In this case, such appropriate measures should be taken as giving the user a warning from the manager by radio, rescuing the user immediately when the user is fainted, or the like.

A air line mask according to the present invention incorporates a detecting means at a position adjacent to an edge section in the downstream side of the collecting means. Thus, it can detect the passage right before the passage is actually generated. The user can take necessary measures between a point of time when the passage is detected and a point of time when the passage is actually generated. This insures higher safety of the air line mask.

In an air line mask according to the present invention, the collecting means are provided in the upstream side as well as in the downstream side, and further a detecting means for detecting poisonous substances is provided between the collecting means in the downstream side. The passage occurs in the collecting means in the upstream side, and the passage is detected by the detecting means. Also, poisonous substances having passed therethrough is collected in the collecting means in the downstream side. Therefore, a certain period of time is required from a point of time when a poisonous material passed through the collecting means in the upstream side until a point of time when the material passed through the collecting means in the downstream side. As a result, the user can take necessary measures with time allowance even if the mask body and the blasting means are located apart from each other. With this feature, higher safety of the air line mask is insured.

In an air line mask according to the present invention, the detecting means for detecting the poisonous material is provided in the downstream side from the collecting means. For this reason a user can take necessary measures after the passage is detected. The necessary measures include replacement of the collecting means and evacuation from the working site. With this configuration, higher safety of the air line mask is insured. In an air line mask according to the present invention, the mask body and the blasting means are provided apart from each other; so that, in a case where the passage is detected in the side of the blasting means, the user is notified of the fact by radio, wire, or the like. With this configuration, the user can know and take necessary measures. As a result, higher safety of the air line mask is insured.

Other objects and features of this invention will become understood from the following description with reference to the accompanying drawings.

DESCRIPTION OF THE PREFERRED EMBODIMENTS

Detailed description is made hereinafter for the present invention with reference to the related drawings. It should be noted that the present invention is not limited by the embodiments described later.

Figure 1:
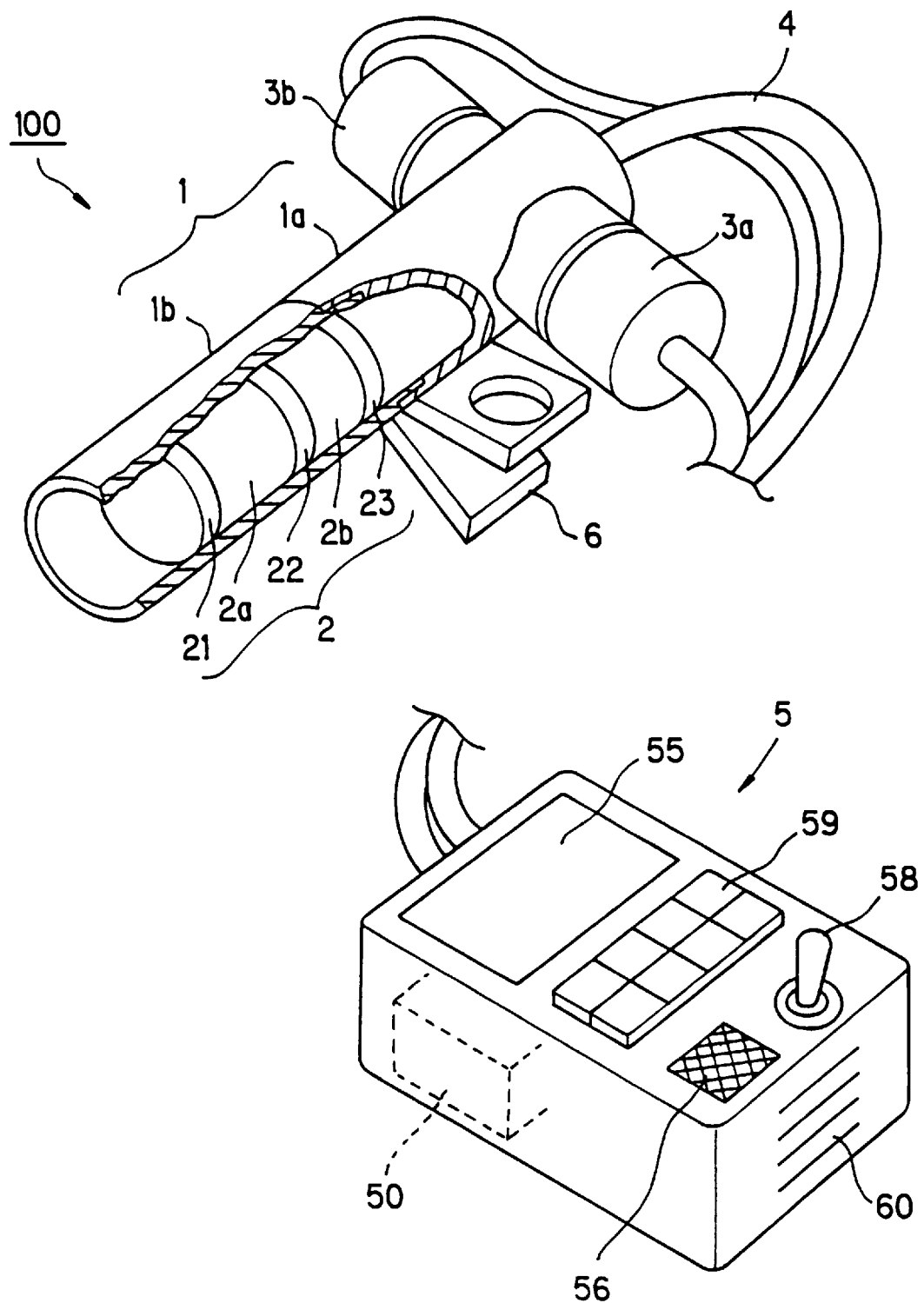
FIG. 1 is a partially broken perspective view showing a solid material collector according to Embodiment 1 of the present invention.

FIG. 1 is a partially broken perspective view showing a solid material collector 100 according to Embodiment 1 of the present invention. An absorbent 2 for absorbing a material to be measured is inserted in a collecting tube 1. Also sensor sections 3a and 3b are provided in the downstream side of the collecting tube 1. The reference numeral 4 indicates a duct 4. An edge of this duct 4 is connected to the edge section in the downstream side of the collecting tube 1. On the other hand, the other edge of the duct 4 is connected to a pump 5 with a control unit. The reference numeral 6 indicates a clip with which the collector is attached onto a user.

The collecting tube is made of Teflon. Commercial activated carbon (produced by Shibata Kagaku) is used for the absorbent 2. The reason is that the activated carbon described above has an excellent absorbing capability to an organic solvent. It should be noted that the absorption characteristics of the activated carbon varies according to a type of carbon or to conditions for activating the carbon. When the activated carbon is used, it is not required to remove moisture in the environmental air, nor to cool the absorbent to enhance a collecting rate. This activated carbon is activated when heated and dehydrated in a dry air or in a nitrogen airflow under the temperature of around 200° C.

Also this activated carbon has a two-layered structure comprising an A-layer 2a and a B-layer 2b. A quantity of activated carbon required for collecting a material to be measured must be set taking into considerations a quantity of an object material for measurement to be recovered. For instance, a quantity of the A-layer 2a in this activated carbon is 100 mg, and that of the B-layer 2b is 50 mg. It should be noted that the A-layer 2a and the B-layer 2b are fixed to the tube with glass wool 21 and polyurethane foam 22, 23. Actually, these grass wool 21, A-layer 2a, polyurethane foam 22, B-layer 2b and polyurethane foam 23 are formed to one package to form the absorbent 2. Accordingly, replacement of the absorbent 2 with a new one is executed with a unit of package.

Other than the activated carbon, silica gel, porous polymer beads, Florisil (a magnesium silicate absorbent), or paper with a specific reagent reactive to a material to be measured impregnated therein may be used. Silica gel is effective in collecting a material to be measured in a polarized gas state. Porous polymer beads are suitable for collecting an unstable chemical compound. Florisil (a magnesium silicate absorbent) is suitable for collecting chlorinated biphenyl (PCB) . Also as paper with a reagent impregnated therein, for instance, paper with 2-pyridilpiperazine impregnated therein is used for measurement of toluene diisocyanate (TDI), and paper with triethanol amine impregnated therein is used for measurement of nitrogen oxides.

Materials to be measured include acetone, methyl ethyl ketone, methanol, isopropylalcohol, methyl acetate, ethyl acetate, dichloromethane, chloroform, 1,1,1-trichloroethane, toluene, and normal hexane or the like. These materials to be measured have weak absorption affinity to activated carbon, and easily pass through the absorbent.

Provided on the operation surface of the pump 5 with a control unit are a display section 55 for displaying passage of a material to be measured through the absorbent or the like, a buzzer 56 for alarming, a power switch 58, and various types of function switches 59. The reference numeral 60 indicates an air outlet port.

Figure 2:
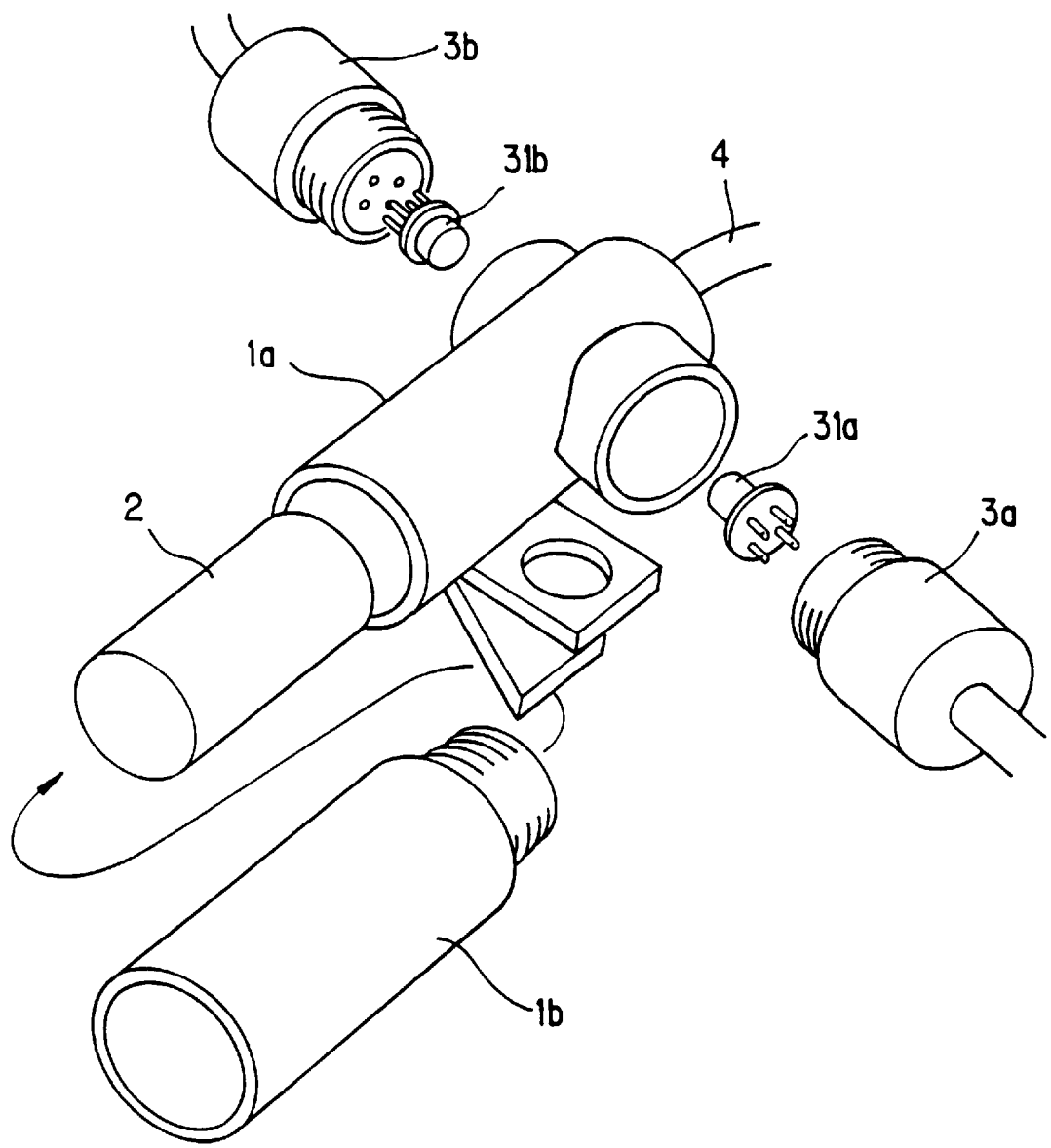
FIG. 2 is an exploded perspective view showing configuration of a solid material collector shown in FIG. 1.

FIG. 2 is an exploded perspective view of the solid material collector 100 shown in FIG. 1. The collecting tube 1 can be divided into a sensor mounting tube 1a for mounting thereonto sensor sections 3a, 3b and an inserting tube 1b for the absorbent 2. The absorbent 2 is inserted into or taken out of the inserting tube in a state in which the inserting tube 1b has been taken out from the collecting tube. The sensor sections 3a, 3b are detachable from the sensor mounting tube 1a. Semiconductor gas sensors 31a, 31b are attached to edge sections of the sensor sections 3a, 3b respectively. These semiconductor gas sensors 31a, 31b are replaceable.

Commercial semiconductor gas sensors developed for monitoring organic solvent vapor (produced by Ricoh Seiki) are used for the semiconductor gas sensors 31a, 31b. The semiconductor gas sensors 31a, 31b have simple configuration with low price, and non-selectively react to almost all types of organic solvent vapor. When a constant current is conducted to the semiconductor gas sensors 31a, 31b and the heaters are heated up, the resistance value is kept constant in clean air. However, when organic solvent vapor is contacted with the surface of the sensor, a semiconductor (n-type oxide such as $SnO_2$, $Fe_2O_3$, ZnO or the like) on the surface of the sensor is reacted with the organic solvent and the resistance value becomes lower.

Change of a resistance value depends on that of a density as described later, so that the density can be determined from the resistance value (a material to be measured can be detected). It should be noted that a gas sensor based on the contact combustion system may be used in place of the semiconductor gas sensor. In this case, a resistance value of the sensor increases according to a reaction of the sensor with the organic solvent, so that the density can be determined from the increased portion of the value.

Figure 3:
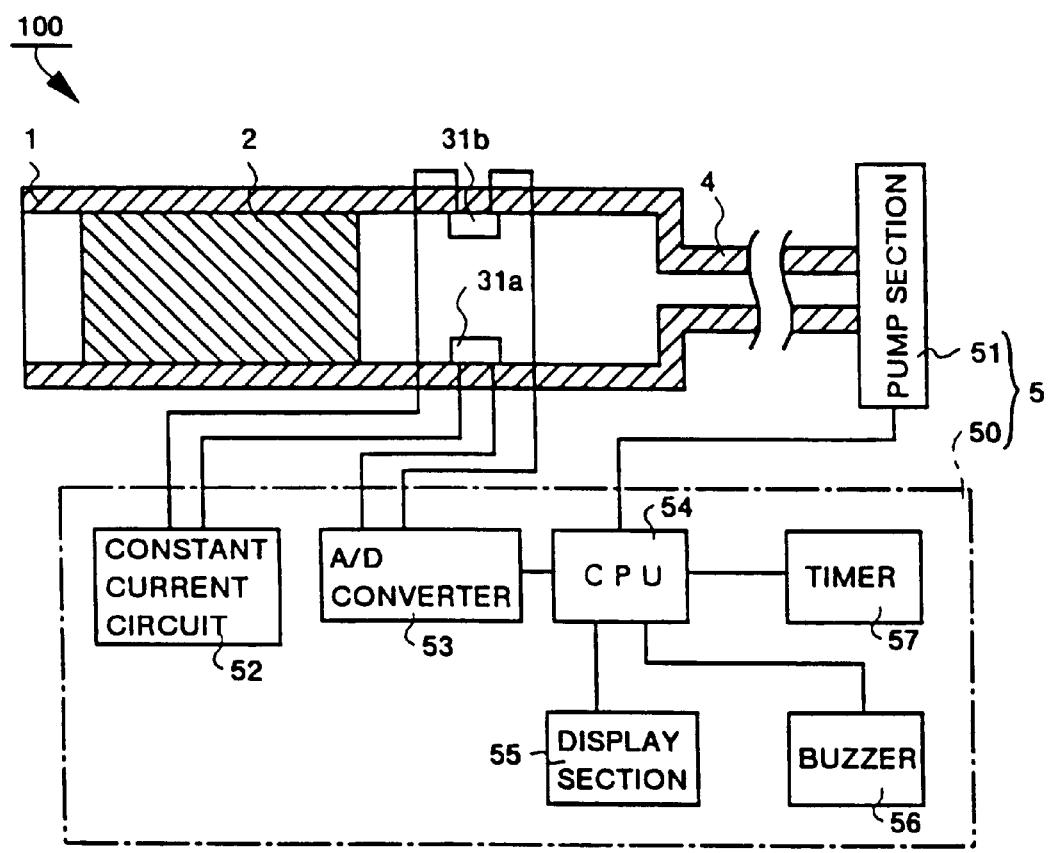
FIG. 3 is a schematic configuration diagram showing configuration of a solid material collector shown in FIG. 1.

FIG. 3 is a schematic block diagram showing configuration of the solid material collector 100 shown in FIG. 1. The pump 5 with a control unit comprises a control section 50 and a pump section 51. The control section 50 comprises a constant-current circuit 52 for feeding a constant current to the heaters in the semiconductor gas sensors 31a, 31b; an A/D converter 53 for subjecting output from the sensors 3a, 3b to A/D conversion; a CPU 54 for executing specified processing according to signals from the A/D converter; a display section 55 for displaying the fact that the passage of a material to be measured through the absorbent has occurred; a buzzer 56 for issuing an alarm to a user; and a timer 57 for measuring a period of time from a point of time when the pump section 51 is started to operate until a point of time when the passage occurs. The pump section 51 sucks a material to be measured with an electric fan, and the sucking force thereof is 0.2 liter/min. The pump section 51 is also supplied with a power from a small-sized rechargeable buttery (not shown herein).

Figure 4:
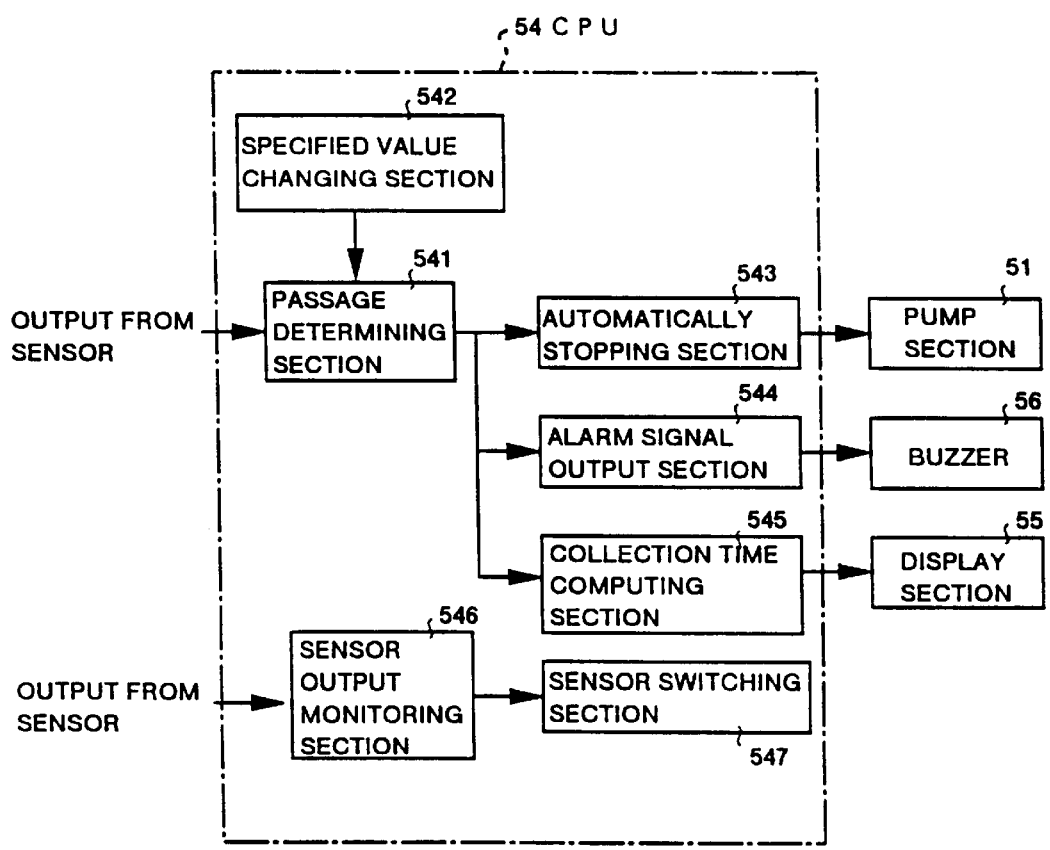
FIG. 4 is a functional block diagram showing functions of a CPU 54 shown in FIG. 3.

FIG. 4 is a functional block diagram showing functions of the CPU 54 shown in FIG. 3. The CPU 54 comprises a passage determining section 541 for determining that the passage of a material to be measured through the absorbent 2 has occurred when resistance values in the semiconductor gas sensors 31a, 31b exceed a specified value described later; a specified value changing section 542 for changing the specified value according to a type of a material to be measured; an automatically stopping section 543 for stopping an operation of the pump section 51 when the passage determining section 541 determines that the passage has occurred; an alarm signal output section 544 for outputting a signal for sounding a buzzer 56 when the passage determining section 541 also determines that the passage has occurred; and an correction time computing section 545 for outputting a measurement signal to the display section 55.

The CPU 54 also comprises a sensor output monitoring section 546 for monitoring dispersion in output from the semiconductor gas sensor 31a (31b); and a sensor switching section 547 for switching the semiconductor gas sensor 31a (31b) to the other semiconductor gas sensor 31b (31a) when dispersion is generated in the output from the sensor.

Figure 5:
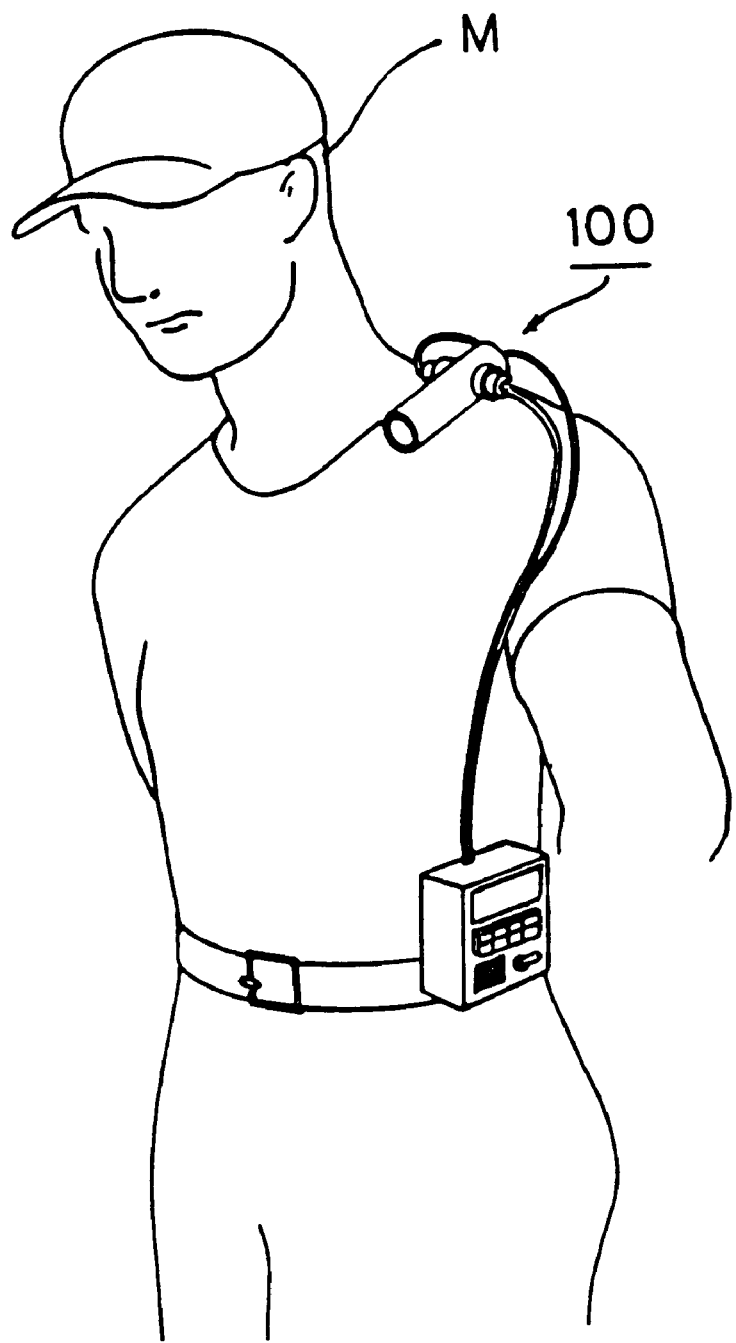
FIG. 5 is an explanatory view showing a state where the of a solid material collector shown in FIG. 1 is set.

FIG. 5 is an explanatory view showing how the solid material collector 100 is attached to a user. The collecting tube 1 is attached with a clip 6 onto a shoulder portion of the clothes which a user M wears. The pump 5 with a control unit is fixed to a belt or the similar position of the user M. The user M works with this solid material collector 900 on.

Figure 6A:
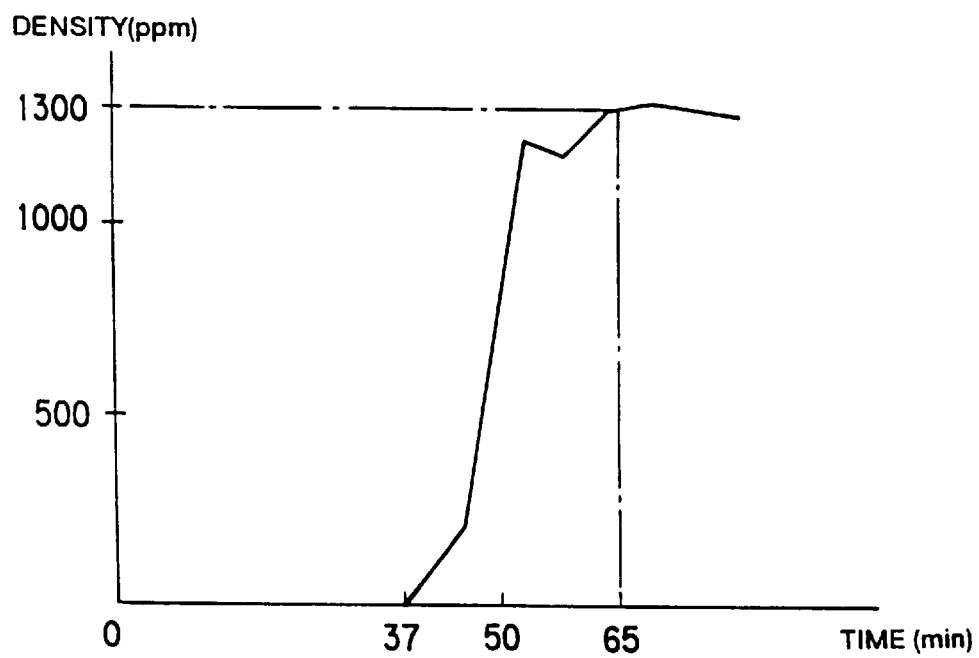
FIG. 6A is a graph showing a relation between time from a start of an experiment and density of a material to be measured.

Next description is made for a method of setting the specified value described above. The specified value is previously obtained through experiments. FIG. 6A is a graph showing a relation between a period of time (minutes) from start of the experiment and a density (ppm) of a material to be measured. The density thereof was measured by analyzing a material to be measured (acetone C33, C37 3/7) passing through the absorbent 2 with the GC. In this experiment, the passage could be recognized in 37 minutes after start of the experiment. Also in 65 minutes after start of the experiment, it was found that the density exceeded 1300 ppm.

Figure 6B:
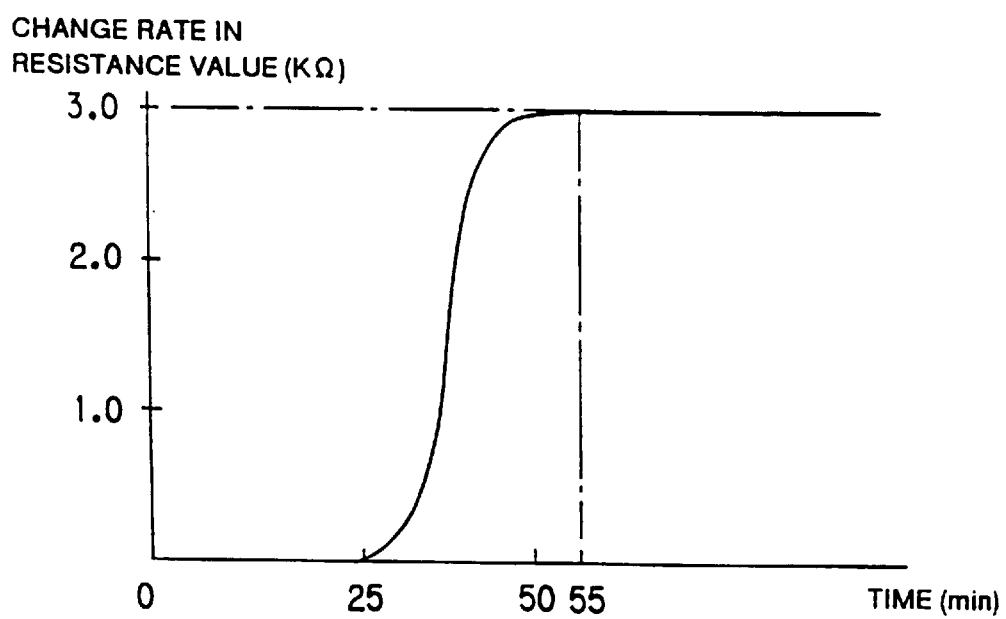
FIG. 6B is a graph showing a relation between time from a start of an experiment and change rate of the resistance value.

FIG. 6B is a graph showing a relation between a period of time (minutes) from start of the experiment and a change rate in the resistance value (KΩ) of the semiconductor gas sensor 31a (31b). The change rate in the resistance value is obtained by sampling the resistance value of the semiconductor gas sensor 31a (31b) in relation to elapse of time. In this experiment, it was found that the resistance value started to become lower in 25 minutes after start of the experiment. Also, in 55 minutes after start thereof, the resistance value became constant. In this experiment, the resistance value lowered by at maximum 3 KΩ due to the passage.

As a result, it was found that the semiconductor gas sensor 31a (31b) could detect the passage earlier than the GC. It is also understood that the change rate in the resistance value in the semiconductor gas sensor 31a (31b) is substantially proportional to that of a density of the material to be measured which passes through the absorbent. For this reason, it is understood that the passage can be detected according to a change rate in a resistance value of the semiconductor gas sensor 31a (31b).

By the way, it is assumed that the specified value is a change rate in a resistance value which does not substantially give any effect over the measurement of the material to be measured. In Embodiment 1, the specified value was set to 0.5 kΩ. It should be noted that the density not substantially effecting the material, for instance in a case where a specified allowable density stipulated by law or the like is 750 ppm, is around +10 ppm. A user inputs this specified value into the collector by operating various types of function switches 59.

Figure 7A:
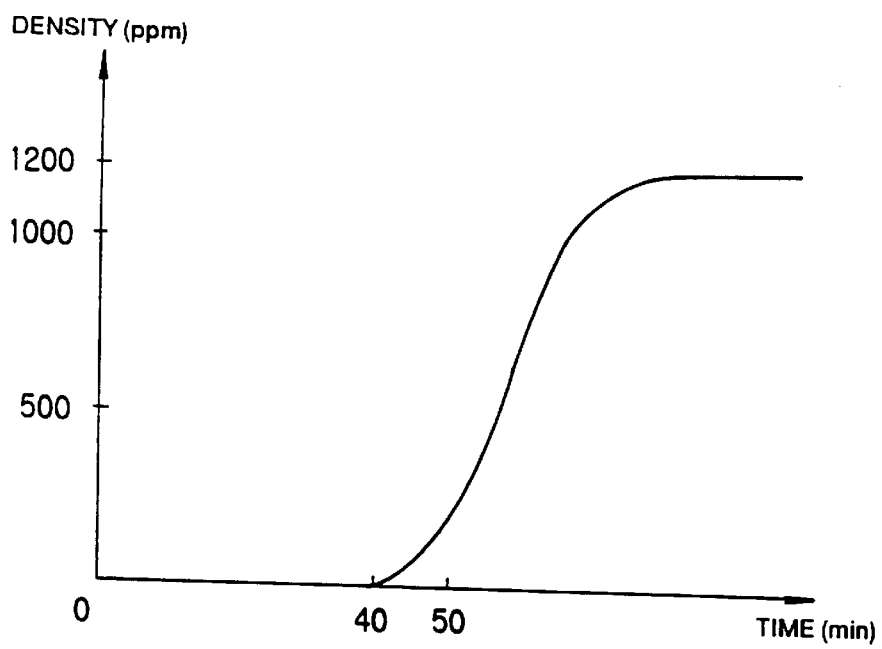
FIG. 7A is a graph showing a relation between time from a start of an experiment and density of the material to be measured in a case where an object material for measurement is trichloroethane.
Figure 7B:
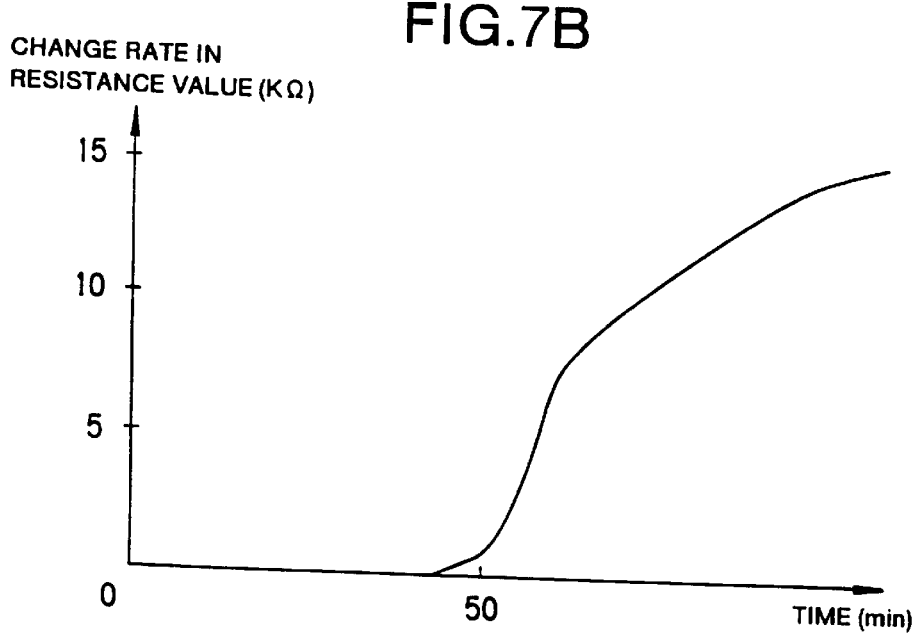
FIG. 7B is a graph showing a relation between time from a start of an experiment and change rate of resistance value.

Sensitivity of the semiconductor gas sensor 31a (31b) to the passage varies according to a material to be measured. For instance, as shown in FIGS. 7A and 7B, in a case where the material to be measured is trichloroethane, a resistance value is changed substantially concurrently when the passage is generated. In this case, unless the specified value is set to a low value, the passage continues, which causes a result of the measurement to be unreliable. The specified value is changed with the specified value changing section 542.

Figure 8:
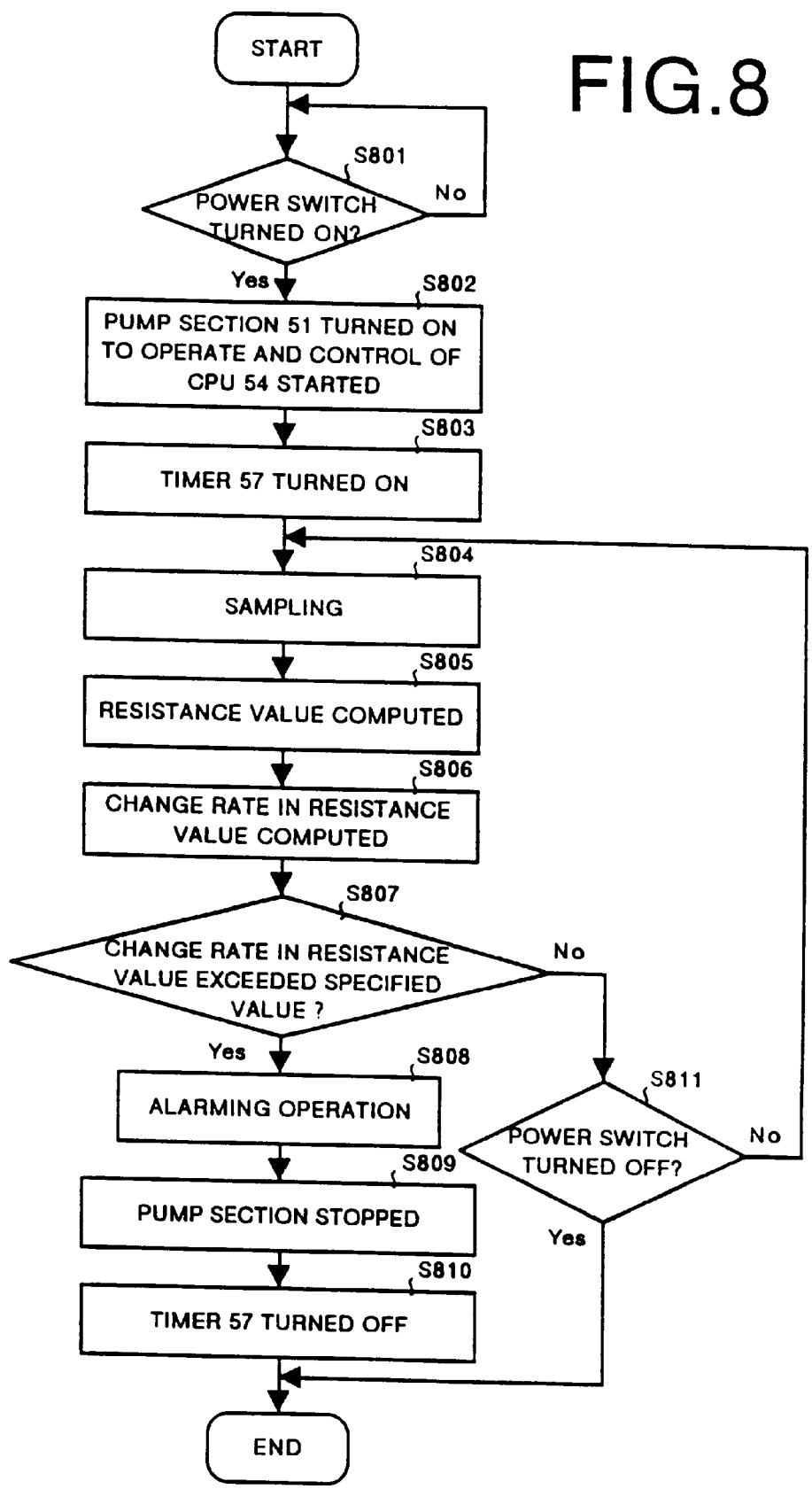
FIG. 8 is a flow chart showing a controlling process with the CPU shown in FIG. 3.

FIG. 8 is a flow chart showing a procedure of controlling the CPU 54 shown in FIG. 3. In step S801, a user turns ON a power switch 58 to start collection of the material to be measured. In step S802, the pump section 51 is started to operate simultaneously when the power switch 58 is turned ON. The material to be measured is introduced into the collecting tube 1 together with the environmental air and collected with the absorbent 2. The air passing through the absorbent 2 is discharged through the duct 4 from the air outlet port 60.

Control of the CPU 54 is started simultaneously when the power switch 58 is turned ON. In step S803, the timer is turned ON simultaneously when the measurement is started to start measuring a period of time for collection. A measurement start signal is transmitted to the collection time computing section 545. A period of time for collection is measured by the collection time computing section 545.

In step S804, a result of detection by the semiconductor gas sensor 31*a* is sampled. A sampling interval is around 30 seconds. In step S805, a resistance value of the semiconductor gas sensor 31*a* is computed from a result of the detection. Subsequently, in step S806, a change rate in the resistance value is computed from the computed resistance value. If the passage is generated, the resistance value of the semiconductor gas sensor 31*a* is changed as shown in FIGS. 6A and 6B.

In step S807, determination is made as to whether the computed change rate in the resistance value has exceeded a specified value or not. The determination is made by the passage determining section 541. The specified value is previously set according to sensitivity of the semiconductor gas sensor 31*a* as described above. This specified value can also be changed according to types of materials to be measured. This change is executed with the specified value changing section 542. If it is determined that the change rate has exceeded the specified value, system control goes to step S808. If it is determined that it has not exceeded the specified value, system control goes to step S811.

In step S808, it is determined that the passage giving substantial effects to a result of the measurement has occurred, and an alarm is issued. The operation for issuing an alarm is executed by the alarm signal output section 544. For instance, a display indicating that the passage has occurred is provided on the display section 55. The buzzer 56 is also sounded. In addition to the means described above, vibration may be given to a user or a lamp for warning may be lit up. In step S809, the pump section 51 is automatically stopped by the automatically stopping section 543. That is because a result of the measurement may become unreliable if the operation for collecting the material is still continued even after the passage is generated. In step S810, the timer 57 is turned OFF to terminate the measurement of the collecting time. Then a measurement end signal is transmitted to the collection time computing section 545.

On the other hand, in step S811, determination is made as to whether the power switch 58 is OFF or not. If it is determined that the power switch 58 is OFF, control of the CPU 54 is terminated. If the power switch 58 is still ON, the control of the CPU 54 is continued. In this case, determination is made that the passage giving substantial effects to a result of the measurement has not been generated because the change rate in the resistance value has not exceeded the specified value. Then the sampling of a result of detection by the semiconductor gas sensor 31*a* is continued until the change rate in the resistance value exceeds the specified value (steps S802 to S807).

By the way, the sensor output monitoring section 546 always monitors dispersion in output from the semiconductor gas sensor 31*a*. Dispersion in output therefrom is generated due to degradation of the semiconductor gas sensor 31*a* after it has been used for a long period of time. When the sensor output monitoring section 546 detects dispersion in output from the semiconductor gas sensor 31*a*, the sensor switching section 547 switches the semiconductor gas sensor 31*a* to the semiconductor gas sensor 31*b*.

It should be noted that this switching is executed by interrupting an output signal from the semiconductor gas sensor 31*a* and inputting thereinto an output signal from the semiconductor gas sensor 31*b*. It should be noted that, when the life of the semiconductor gas sensor 31*b* is over, the sensor sections 3*a* and 3*b* are taken out from the sensor mounting tube 1*a*, and are replaced with new semiconductor gas sensors 31*a* and 31*b*. The life thereof is displayed on the display section 55. Also, when the life thereof is over during the operation for collection, the buzzer 56 is sounded to let a user know about the fact.

Next description is made for a method of measuring the density. When the operation for collecting materials to be measured is completed, the inserting tube 1*b* is taken out from the collecting tube 1 as shown in FIG. 2, and adsorbents 2 are taken out by pushing them out from the inserting tube 1*b*. Then the materials to be measured collected by each of adsorbents 2 are separated from each other and quantified according to the GC.

Herein, a volume of the environmental air sucked by the pump section 51 is computed from the collecting time measured by the collection time computing section 545 as well as from the flow rate of the air from the pump section 51. In a case where the control of the pump section 51 to be automatically stopped is reset and the materials are continued to be collected although the passage has been generated, the quantification is executed in consideration of the collecting time measured by the collection time computing section 545. For instance, if it is determined that the passage has continued for 10 minutes, the quantification is executed without considering a volume of the environmental air sucked by the pump section 51 during the period of time.

Next description is made for replacement of adsorbents 2. At first, an absorbent 2 is pushed into the inserting tube 1*b*.

Then the inserting tube 1*b* is mounted onto the sensor mounting tube 1*a*. It should be noted that, when different materials to be measured are collected, any absorbent 2 appropriate for the purpose should be selected. A procedure of the replacement is the same as that in a case of activated carbon.

Figure 9:
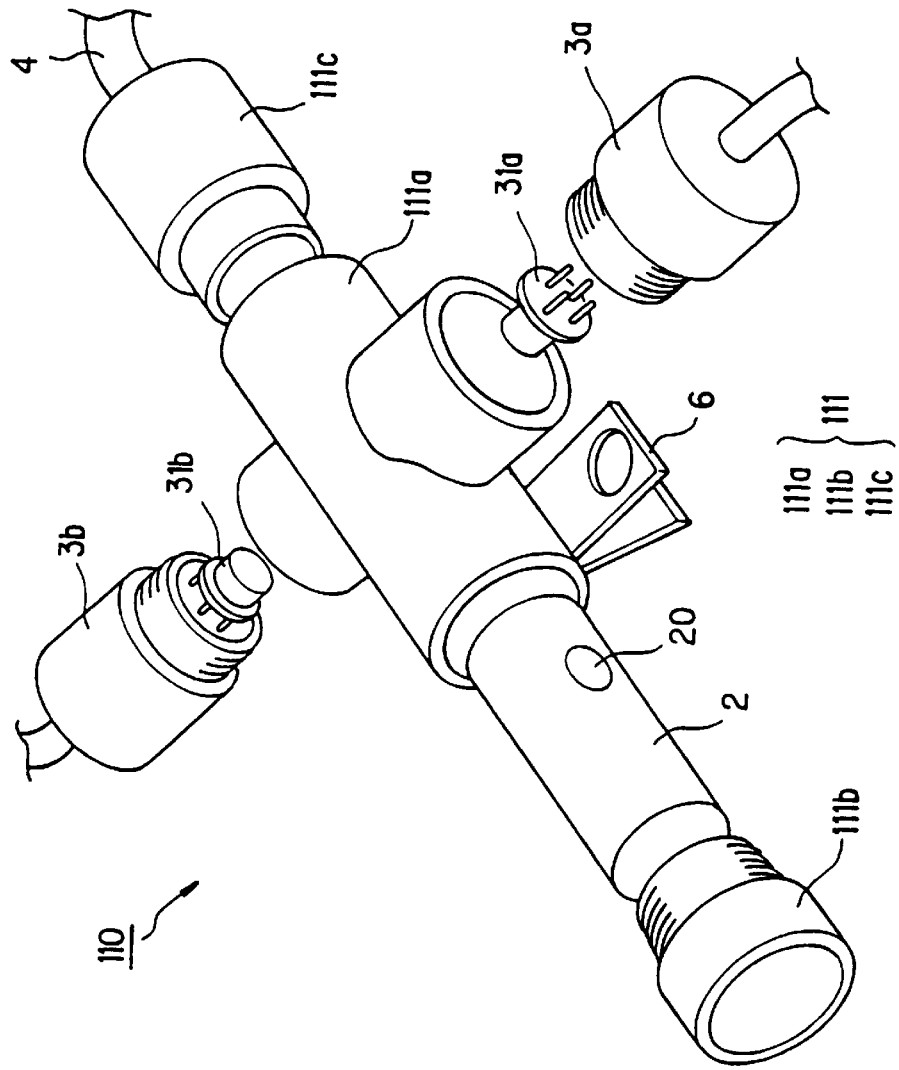
FIG. 9 is an exploded perspective view showing Variant 1 of the solid material collector shown in FIG. 1.

FIG. 9 shows variant 1 of the solid material collector 100 shown in FIG. 1. The solid material collector 110 is characterized in that the semiconductor gas sensors 31*a* and 3 1*b* are incorporated at positions each adjacent to an edge in the downstream side of the absorbent 2. The collecting tube 111 has a construction in which the tube 111 can be divided into three sections; a mounting tube 111*a* for inserting thereinto an absorbent 2, an upstream side fixing tube 111*b* for fixing the absorbent 2 from the upstream side of the collecting tube 111, and a downstream side fixing tube 111*c* for fixing the absorbent 2 from the downstream side thereof. The absorbent 2 is inserted into and taken out from the mounting tube 111a in a state in which the upstream side fixing tube 111b and the downstream side fixing tube 111c have been disengaged from the mounting tube 111a.

The sensor sections 3a, 3b are mounted onto the mounting tube 111a. The sensor sections 3a, 3b are also detachable from the mounting tube 111a. Semiconductor gas sensors 31a, 31b are attached to edges in the sensor sections 3a, 3b respectively. These semiconductor gas sensors 31a, 31b are replaceable.

A duct 4 is attached to an edge of the downstream side fixing tube 111c. This duct 4 is connected to a pump 5 with a small-sized electric control unit (Refer to FIG. 1, not shown in FIG. 9). The reference numeral 6 indicates a clip for attaching the tube to a user. The configuration other than the sections described above is the same as that in the solid material collector 100.

The solid material collector 110 is assembled as follows. At first, the absorbent 2 is inserted into the mounting tube 111a. At this point of time, sensor holes 20 of the absorbent 2 are positioned in the direction of the sensor sections 3a, 3b respectively. Then the sensor sections 3a, 3b are mounted to the mounting tube 111a. At this point of time, the semiconductor gas sensors 31a, 31b are positioned so that the header sections thereof are inserted in the sensor holes 20 respectively. Then, the upstream side fixing tube 111b and the downstream side fixing tube 111c are mounted to the mounting tube 111a.

The absorbent 2 is fixed with edge surfaces of screw sections in the upstream side fixing tube 111b and in the downstream side fixing tube 111c respectively. The absorbent 2 is replaced with a new one according to the same procedure as described above after the collector is disassembled once. It should be noted that, considering easiness in replacement of adsorbents, the sensor hole 20 described above may be formed with a key-hole shape. Also, when it is used, this solid material collector 110 is attached to a user with the clip 6. The collecting work by the solid material collector 110 is executed in the same manner as that in a case of the solid material collector 100 described above (Refer to FIG. 8).

With the solid material collector 110 described above, the semiconductor gas sensors 31a, 31b are incorporated at positions each adjacent to an edge in the downstream side of the absorbent 2, so that materials to be measured can be detected immediately before the passage is actually generated. As a result of this feature, the measurement can more accurately be executed.

Figure 10:
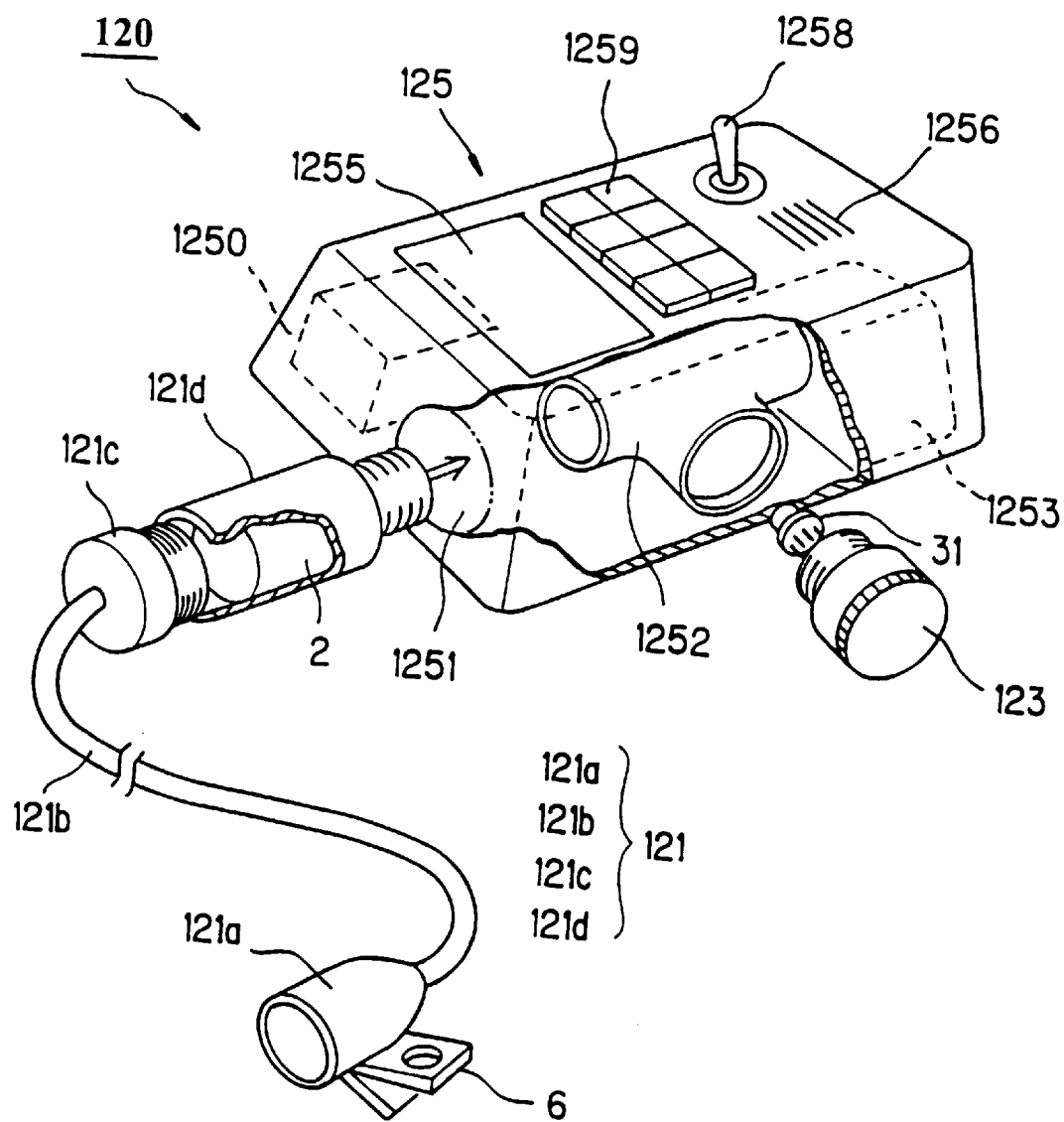
FIG. 10 is a partially broken sectional perspective view showing Variant 2 of the solid material collector shown in FIG. 1.

A portion of the collecting tube and a sensor section or the like may be integrated with each other in the pump side. FIG. 10 shows Variant 2 of the solid material collector 100 shown in FIG. 1. The reference numeral 121 indicates a collecting tube. This collecting tube 121 comprises an introducing section 121a for attaching the tube onto the shoulder portion of the clothes a user wears, an absorbent fixing section 121c connected to the introducing section 121a with a duct section 121b, and a collecting section 121d incorporating therein an absorbent 2. The reference numeral 6 indicates a clip for attaching the tube to the user.

The reference numeral 125 indicates a pump with a small-sized electric control unit. A collecting tube attaching section 1251 for attaching the collecting tube 121 inside the pump is provided in the upper side of this pump 125 with the control unit. A sensor section 123 is provided on the side face of the pump 125 with the control unit. A semiconductor gas sensor 31 is attached to an edge of this sensor section 123. This semiconductor gas sensor 31 is replaceable.

Provided on the operation face of the pump 125 with the control unit are a display section 1255 for displaying the passage or the like, a buzzer 1256 for alarming, a power switch 1258, and various types of function switches 1259. The reference numeral 1250 indicates a control section. The reference numeral 1252 indicates an internal tube. The sensor section 123 is attached to the side section of the internal tube 1252. The edge of the semiconductor gas sensor 31 is projected into the internal tube 1252 with the sensor section 123 attached thereto. The reference numeral 1253 indicates a pump section.

The absorbent 2 and semiconductor gas sensor 31 used in Variant 2 are the same as those used for the solid material collector 100. The solid material collector 120 of Variant 2 has also the same configuration as that of in the solid material collector 100 (Refer to FIG. 3).

Next description is made for assembling the absorbent 2. At first, the absorbent 2 is inserted into the collecting section 121d. Then, the absorbent fixing section 121c is attached to the collecting section 121d for fixing the absorbent 2 thereto. The sensor section 123 is previously attached to the pump 125 with the control unit. The semiconductor gas sensor 31 is positioned in the internal tube 1252 with the sensor section 123 attached to the pump. Then, the collecting tube 121 is attached to the internal tube 1252 by inserting thereinto the collecting tube from the collecting tube attaching section 1251.

The semiconductor gas sensor 31 is positioned in the downstream side of the absorbent with the collecting tube 121 having been attached to the internal tube. The absorbent 2 is replaced with a new one according to the same procedure as described above after the tube is once disassembled. Also when it is used, this solid material collector 120 is attached to a user with the clip 6. The operation for collection by the solid material collector 120 is executed in the same manner as that in a case of the solid material collector 100 described above (Refer to FIG. 8).

With the solid material collector 120 described above, the collector can be constructed with a compact size. Also, only the introducing section 121a is attached to the shoulder portion of the user, so that the user can work without any load thereon. Also the user does not feel the collector to be a nuisance.

Figure 11:
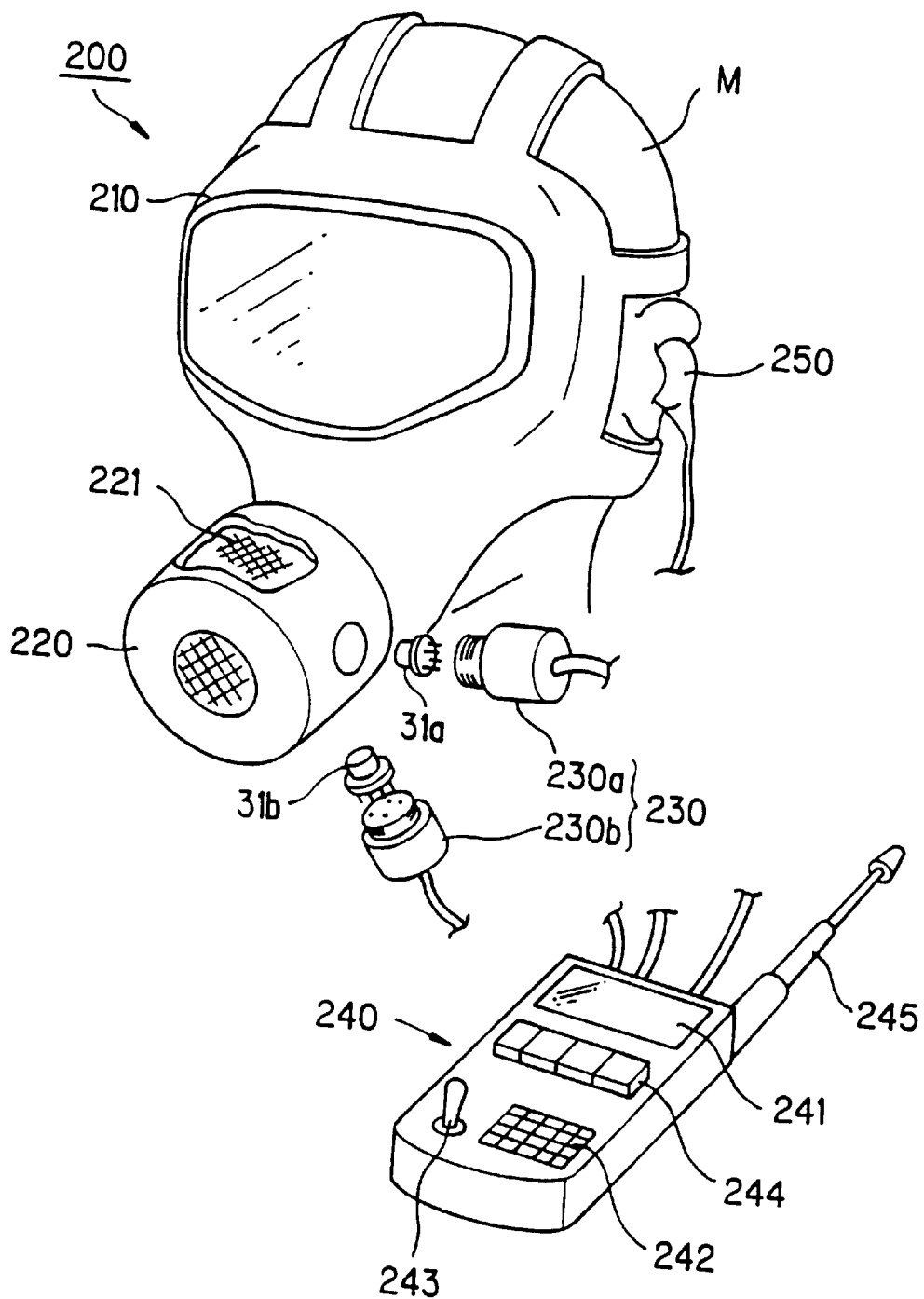
FIG. 11 is a perspective view showing a gas mask according to Embodiment 2 of the present invention.

FIG. 11 is a perspective view showing a gas mask according to Embodiment 2 of the present invention. This gas mask 200 is so called a direct coupled type one and comprises a rubber mask body 210 subjected to halogen-processing for putting on the face of the user, an absorbing can 220 for absorbing external poisonous substances, a sensor section 230 detachably provided in the absorbing can 220, a control unit 240 for executing specified processing according to an output from the sensor section 230, and an earphone 250 connected to the control unit 240 for alarming the user to the materials.

The absorbing can 220 is possible to be replaced with one according to a type of substance to be absorbed. A absorbent 221 is packed in the absorbent can 220. Any absorbent 221 appropriate for poisonous substances in the working site should be selected. For instance, activated carbon is selected for collecting organic gas. Also, in addition to activated carbon, silica gel, porous polymer beads, Frolysil, or paper with a specific reagent reactive to a poisonous substance impregnated therein may be used.

A poisonous substance includes halogen gas, sour gas, organic gas, carbon monoxide, ammonia, sulfur dioxide, sulfur, hydrocyanic acid, hydrogen sulfide, methyl bromide, and phostkin.

Semiconductor gas sensors 31a, 31b are attached to edge sections of sensor sections 230a, 230b respectively. These semiconductor gas sensors 31a, 31b are the same as those used in Embodiment 1. A gas sensor based on the contact combustion system may be used in place of the semiconductor gas sensor.

Provided on the operation face of the control unit 240 are a display section 241 for displaying passage or the like, a buzzer 242 for alarming, a power switch 243, and various types of function switches 244. An antenna 245 for transmitting the fact that the absorbent is passed through with the poisonous substances to an external device and a terminal of an earphone 250 or the like are provided on the upper side of the control unit 240.

Figure 12A:
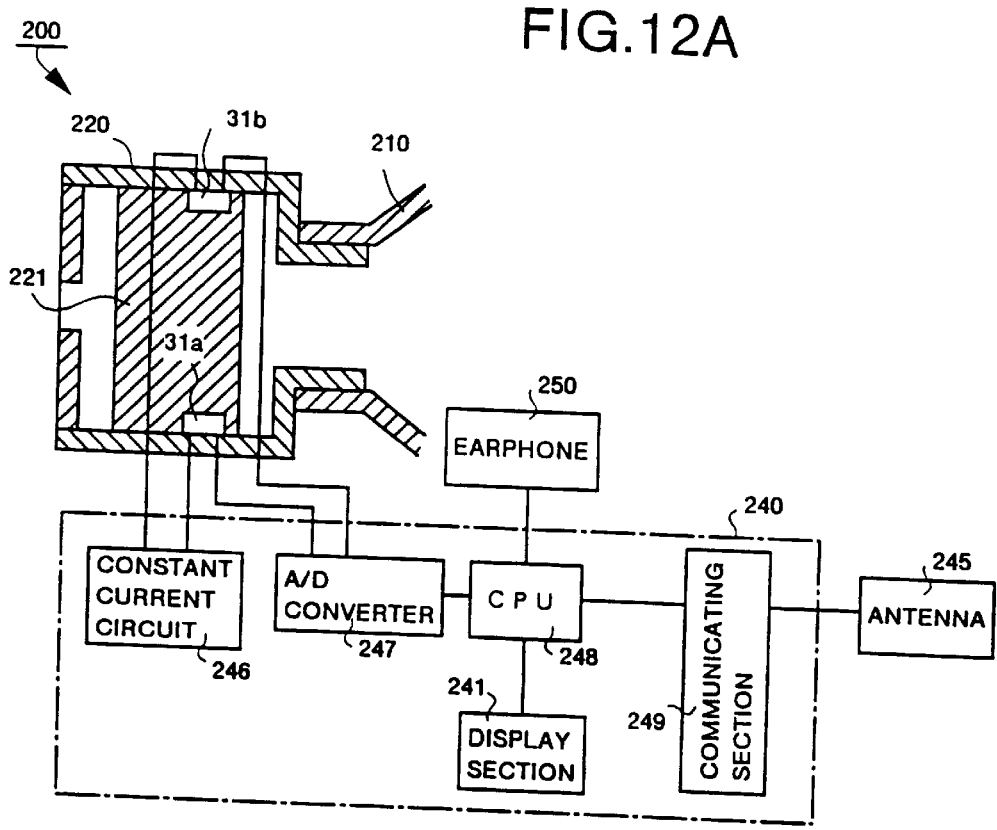
FIG. 12A is a view showing general configuration of the gas mask shown in FIG. 11.

FIG. 12A is a schematic block diagram showing configuration of the gas mask 200 shown in FIG. 11. The control unit 240 comprises a constant-current circuit 246 for feeding a constant current to heaters in the semiconductor gas sensors 31a, 31b; an A/D converter 247 for subjecting output from the sensor 230a, 230b to A/D conversion; a CPU 248 for executing a specified processing according to signals from the A/D converter 247; a communicating section 249 for notifying the state of passage or the like to an external managing system 280 and receiving signals from the external managing system 280; and a display section 241. The semiconductor gas sensors 31a, 31b are incorporated at positions each adjacent to inside the mask body in the absorbent 221. The reason is that the passage is detected before it actually occurs.

Figure 12B:
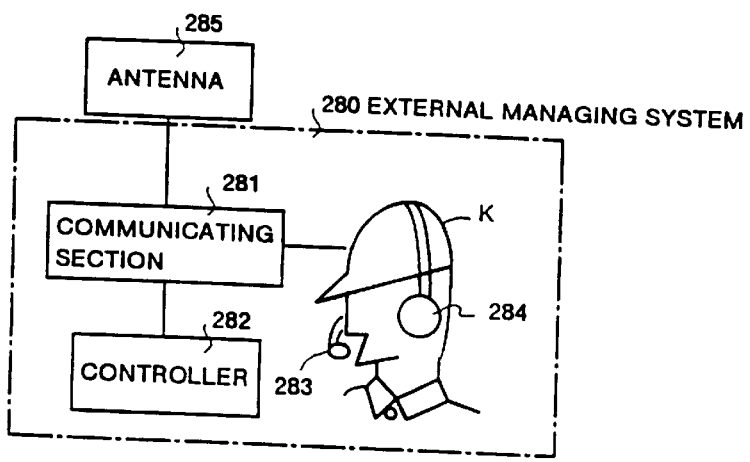
FIG. 12B is a view showing general configuration of an external controlling system for controlling a user of the gas mask shown in FIG. 11 from outside.

FIG. 12B is a schematic block diagram showing configuration of the external managing system 280 for managing a user with the gas mask 200 on from outside. This external managing system 280 comprises a communicating section 281 capable of communicating with the user with the gas mask 200 on through the communicating section 249; a controller 282 for operating communications; and a microphone 283 as well as a head phone 284 each of which a manager K wears. The reference numeral 285 indicates an antenna.

Figure 13:
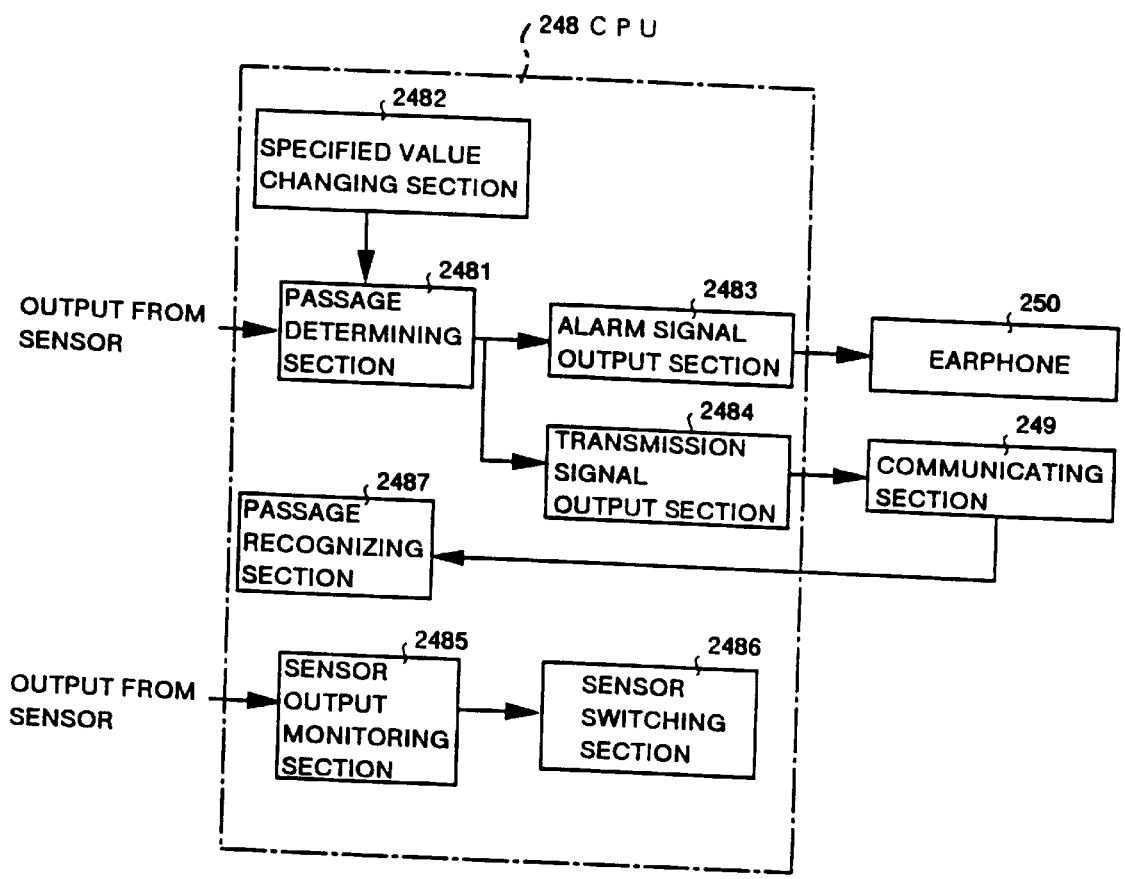
FIG. 13 is a functional block diagram showing a function of the CPU shown in FIGS. 12A and 12B.

FIG. 13 is a functional block diagram showing functions of the CPU 248 shown in FIGS. 12A and 12B. The CPU 248 comprises a passage determining section 2481 for determining that the passage is generated in the absorbent 2 when resistance values of the semiconductor gas sensors 31a, 31b each exceed a specified value; a specified value changing section 2482 for being capable of changing the specified value according to types of poisonous substances; an alarm signal output section 2483 for outputting an alarm signal to an earphone 250 when the passage determining section 2481 determines that the passage is generated; and a transmission signal output section 2484 for transmitting a signal, when the passage determining section 2481 determines that the passage is generated, for the fact to the external managing system 280.

The CPU 248 also comprises a sensor output monitoring section 2485 for always monitoring dispersion in output from the semiconductor gas sensor 31a (31b); and a sensor switching section 2486 for switching the semiconductor gas sensor 31a (31b) to the other semiconductor gas sensor 31b (31a) when dispersion is generated in the output from the sensor. The CPU 248 further comprises a passage recognizing section 4287 for determining whether the manager K in the external managing system 280 recognizes the fact that the passage has been generated or not.

Figure 14:
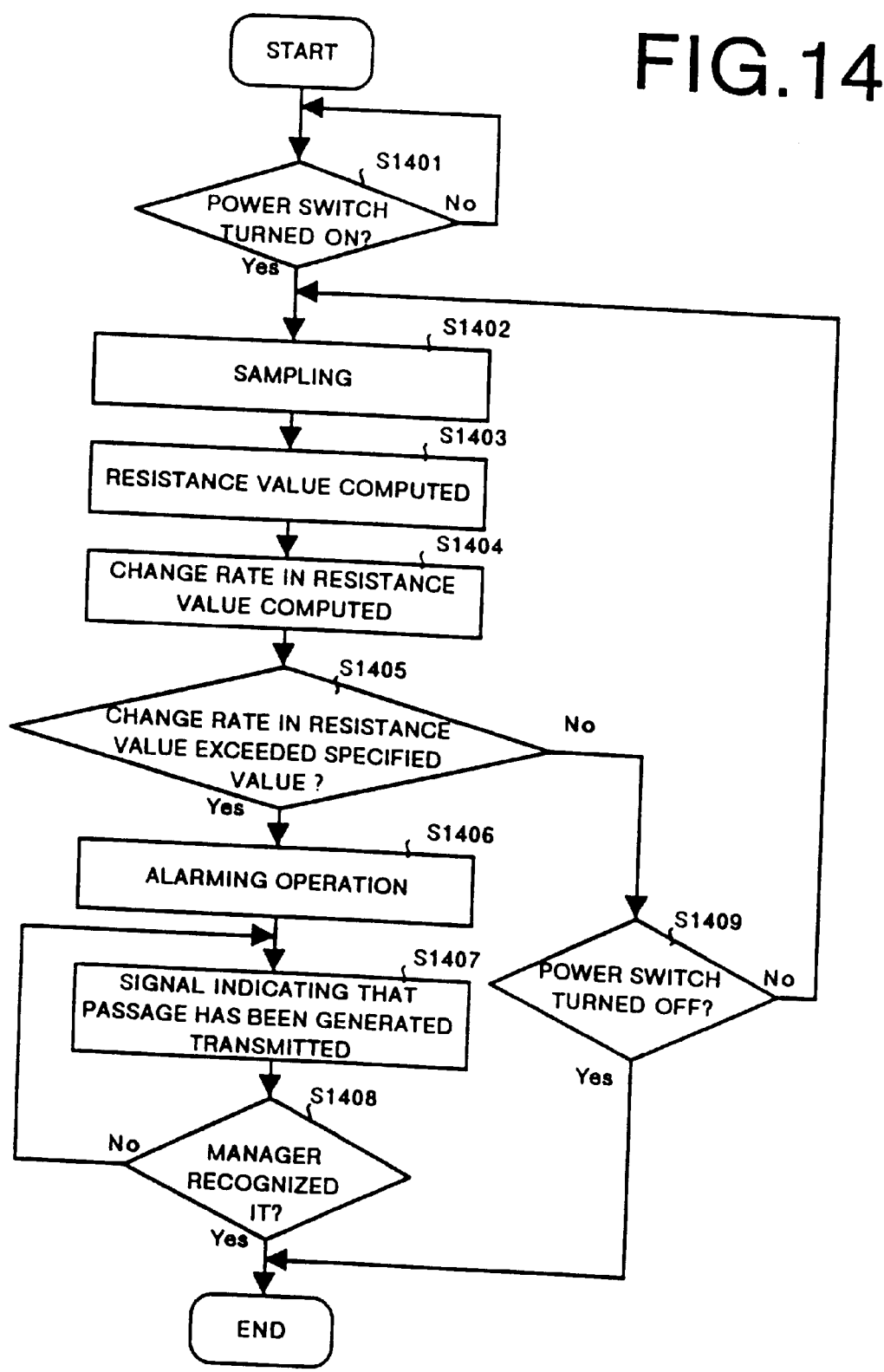
FIG. 14 is a flow chart showing a controlling process with a CPU shown in FIGS. 12A and 12B.

FIG. 14 is a flow chart showing a procedure of controlling the CPU 248 shown in FIGS. 12A and 12B. In step S1401, a user turns ON the power switch 243. Controlling of the CPU 248 is started simultaneously when the power switch 243 is turned ON, which makes it possible to execute communications with the external managing system 280.

In step S1402, a result of detection executed by the semiconductor gas sensor 31a is sampled. A sampling interval is around 30 seconds. In step S1403, a resistance value of the semiconductor gas sensor 31a is computed from the result of the detection. Then, in step S1404, a change rate in the resistance value is computed from the computed resistance value. If the passage is generated, the resistance value of the semiconductor gas sensor 31a is changed (Refer to FIG. 6).

In step S1405, determination is made as to whether the computed change rate in the resistance value has exceeded a specified value or not. This determination is made by the passage determining section 2481. The specified value is previously set according to the sensitivity of the semiconductor gas sensor 31a as shown in Embodiment 1. Also, it is desirable to change this specified value according to any of poisonous substances as required. This change is executed by the specified value changing section 2482. If it is determined that the change rate has exceeded the specified value, system control goes to step S1406. If it is determined that the change rate has not exceeded the specified value, system control goes to step S1409.

In step S1406, if it is determined that the passage has been generated, an operation for issuing an alarm is executed. The alarming operation is executed according to a signal from the alarm signal output section 2483. For instance, the fact that the passage has been generated is displayed on the display section 241. A warning beep is given to a user through the earphone 250. In addition to the means described above, vibration may be given to the user or a lamp for alarming may be lit up.

In step S1407, the CPU transmits a signal indicating that the passage has been to the external managing system 280. The transmission signal output section 2484 outputs the signal indicating that the passage has been generated from the communicating section 249. This output signal is received by the communicating section 281 in the external managing system 280. The signal received by the communicating section 281 and indicating that the passage has been generated is transmitted to the manager K. For instance, to whom the passage has been generated is notified to the manager by means of a warning beep through the head phone 284 or of announcement with an audio signal.

In step S1408, determination is made as to whether the manager K has recognized the fact that the passage has been in the gas mask 200 or not. This determination is made by the passage determining section 2487. More specifically, the manager K operates the controller 282 to transmit a signal for recognition from the communicating section 281 in the external managing system 280 side. The communicating section 249 in the gas mask side receives this signal. The received signal is sent to the passage recognizing section 2487 for recognition. On the other hand, in a case where the recognition signal can not be received, the communicating section 249 continues to output the signal indicating that the passage has been generated to the passage recognizing section until the manager K notices it (step S1407, step S1408).

On the other hand, in step S1409, determination is made as to whether the power switch 243 is OFF or not. If it is determined that the power switch 243 is OFF, control of the CPU 248 is terminated. If it is determined that the power switch 243 is still ON, the control of the CPU 248 is continued. In this case, determination is made that the passage has not been generated because the change rate in the resistance value of the semiconductor gas sensor 31*a* has not exceeded the specified value. Then the sampling of a result of detection by the semiconductor gas sensor 31*a* is continued until the change rate in the resistance value exceeds the specified value (steps S1402 to S1405).

When the user does not stop the work even although the passage has been generated, the manager K may call the user to stop the work through the microphone 283. The voice of the manager K is transmitted to the user through the earphone 250.

The sensor output monitoring section 2485 always monitors dispersion in output from the semiconductor gas sensor 31*a*. The dispersion in output therefrom is generated due to degradation of the semiconductor gas sensor 31*a* after it has been used for a long period of time. When the sensor output monitoring section 2485 detects dispersion in output from the semiconductor gas sensor 31*a*, the sensor switching section 2486 switches the semiconductor gas sensor 31*a* to the semiconductor gas sensor 31*b*.

It should be noted that this switching is executed by interrupting an output signal from the semiconductor gas sensor 31*a* and inputting thereinto an output signal from the semiconductor gas sensor 31*b*. At the point of time when the life of the semiconductor gas sensor 31*b* is over, the sensor sections 230*a* and 230*b* are taken out from the sensor mounting tube 1*a*, and are replaced with new semiconductor gas sensors 31*a* and 31*b*. The life thereof is displayed on the display section 241. Also, when the life thereof is ended while the user is working with it, it is notified to the user through the earphone 250.

Figure 15:
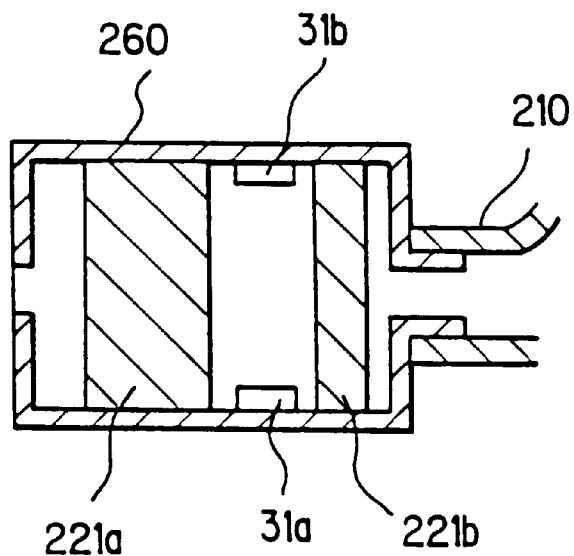
FIG. 15 is a view showing general configuration of Variant 1 of the gas mask shown in FIG. 11.

FIG. 15 is a schematic block diagram showing Variant 1 of the gas mask 200 shown in FIG. 11. A two-layered absorbent having an absorbent 221*a* in the upstream side and that 221*b* in the downstream side is packed in an absorbing can 260. Semiconductor gas sensors 31*a*, 31*b* are provided between the absorbent 221*a* and that 221*b*. Other configuration of variant 1 is the same as that in the gas mask 200.

As described above, the mask has a two-layered absorbent 221, and the semiconductor gas sensors 31*a*, 31*b* are provided therebetween, so that the passage is generated in the absorbent 221*a* in the upstream side, which is detected by the semiconductor gas sensors 31*a*, 31*b*. After the passage is detected by the semiconductor gas sensors 31*a*, 31*b*, the working is stopped. Any of the poisonous substances which passes through the absorbent is absorbed by the absorbent 221*b* in the downstream side. For this reason, the user will never absorb any poisonous substances which pass therethrough.

Figure 16:
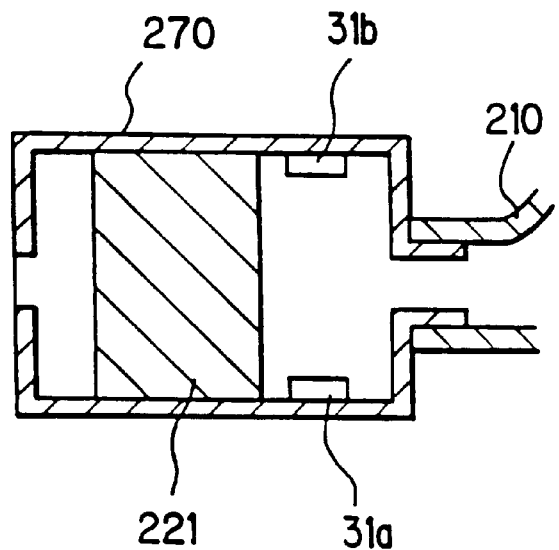
FIG. 16 is a view showing general configuration of Variant 2 of the gas mask shown in FIG. 11.

FIG. 16 is a schematic block diagram showing Variant 2 of the gas mask 200 shown in FIG. 11. The absorbent 221 is packed in an absorbing can 270. Semiconductor gas sensors 31*a*, 31*b* are provided in the downstream side of the absorbent 221. Other configuration of Variant 2 is the same as that in the gas mask 200.

As described above, provision of the semiconductor gas sensors 31*a*, 31*b* in the downstream side of the absorbent 221 makes the configuration of the gas mask simpler. Also the manufacturing is made easier, whereby a low price device can be obtained.

Figure 17:
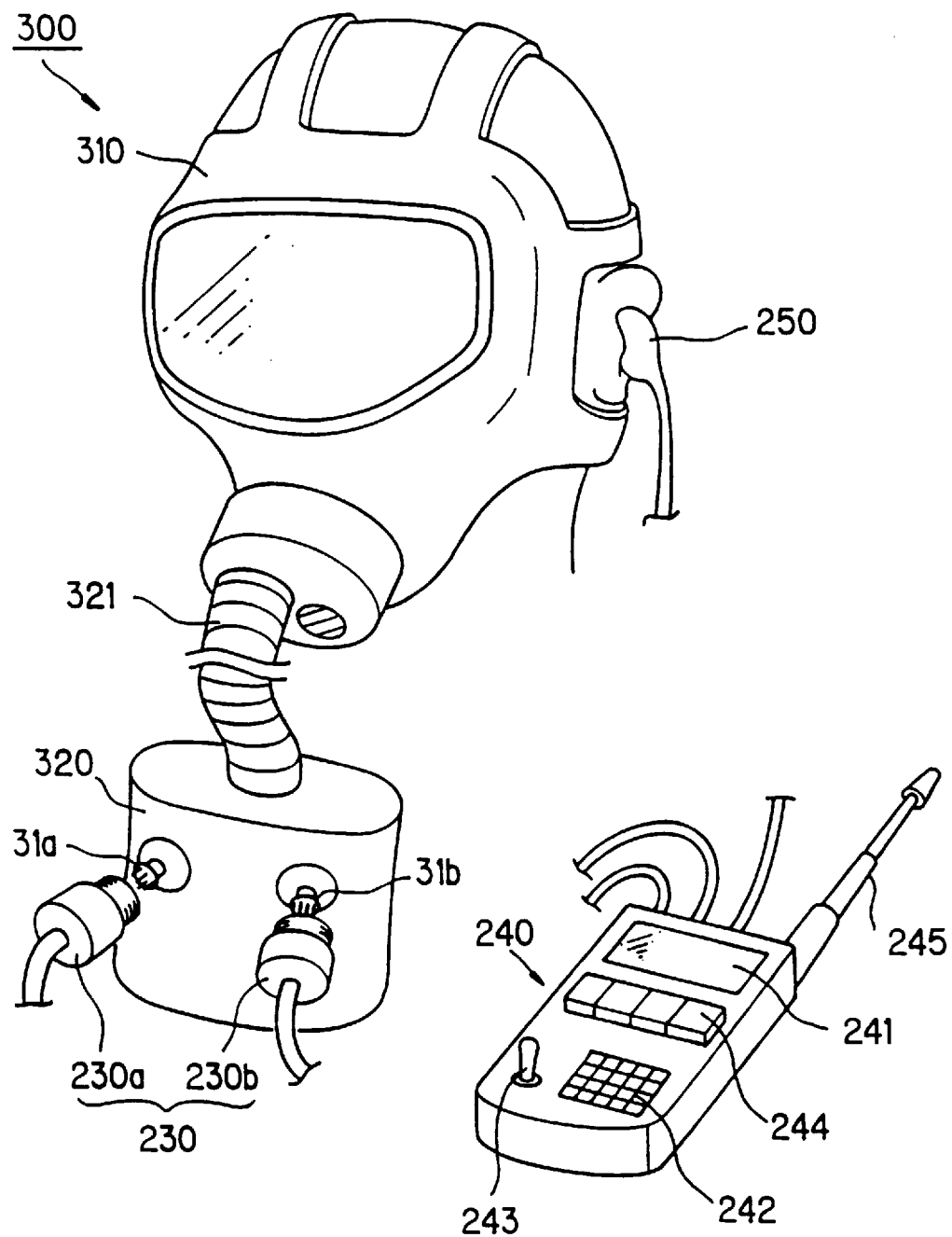
FIG. 17 is a perspective view showing Variant 3 of the gas mask shown in FIG. 11.

A gas mask is not necessarily of a direct coupled type like the gas mask 200, and one based on the isolated type may be used. FIG. 17 is a perspective view showing Variant 3 of the gas mask 200 shown in FIG. 11. This gas mask 300 is so-called an isolated type one and comprises a rubber mask body 310 subjected to halogen processing for putting on the face of the user, an absorbing can 320 coupled to the mask body 310 through a hose 321 for absorbing external poisonous substances, a sensor section 230 detachably provided in the absorbing can 320, a control unit 240 for executing specified processing according to an output from the sensor section 230, and an earphone 250 connected to the control unit 240 for alarming the user to the materials.

This absorbing can 320 has a capacity larger than that in the direct coupled type of gas mask 200. The absorbing can 320 can absorb a larger quantity of poisonous substances. And for this reason, the absorbing can 320 can be used in adverse working environments. Semiconductor gas sensors 31*a*, 31*b* are attached to edges of the sensor sections 230*a*, 230*b* respectively. These semiconductor gas sensors 31*a*, 31*b* are the same as those in Embodiment 1.

Other configuration of Variant 3 is the same as that in the gas mask 200. With this gas mask 300, a user can work more safely even in hostile working environments.

Figure 18:
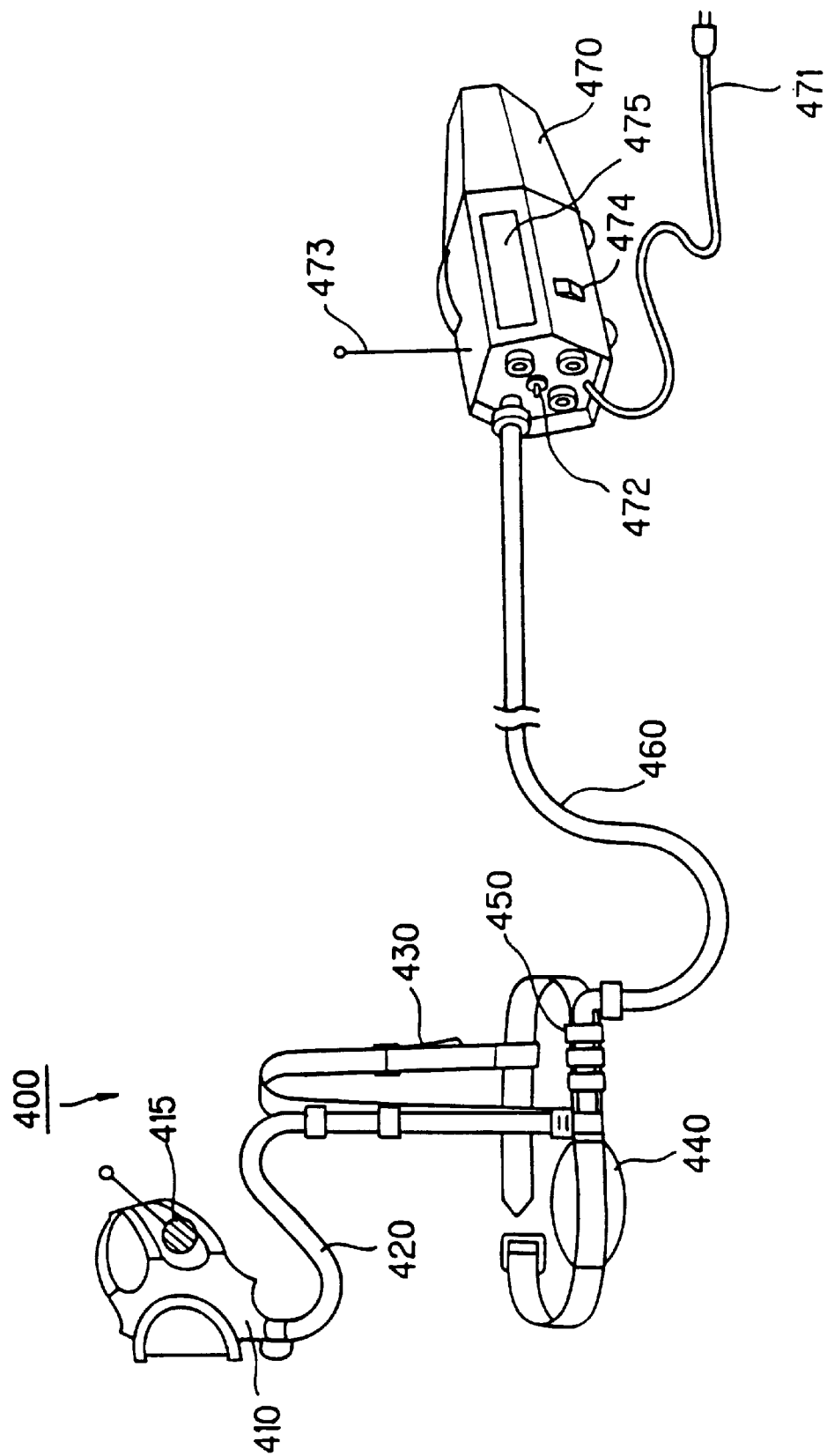
FIG. 18 is a perspective view showing an air line mask according to Embodiment 3 of the present invention.

FIG. 18 is a perspective view showing an air line mask according to Embodiment 3 of the present invention. This air line mask 400 comprises a mask body 410 for putting on the face of a user, a communicating unit 415 which the user puts on, a communicated pipe 420 coming out from the mask body 410, a harness 430 for fixing the communicated pipe 420 to the body of the user, an air adjusting bag 440 provided at the edge of the communicated pipe 420 for adjusting air to be sent, a flow rate adjusting device 450 provided at the edge of the same communicated pipe 420 for adjusting air to be sent to an appropriate airflow, and an electric blower 470 coupled to the flow rate adjusting device 450 through the hose 460. In the figure, designated at the reference numeral 471 is a power code, at 472 an airflow select switch, and at 473 an antenna.

A power switch 474 and a display section 475 for displaying the state of passage or the like are provided on the side face of the housing of the electric blower 470.

Figure 19:
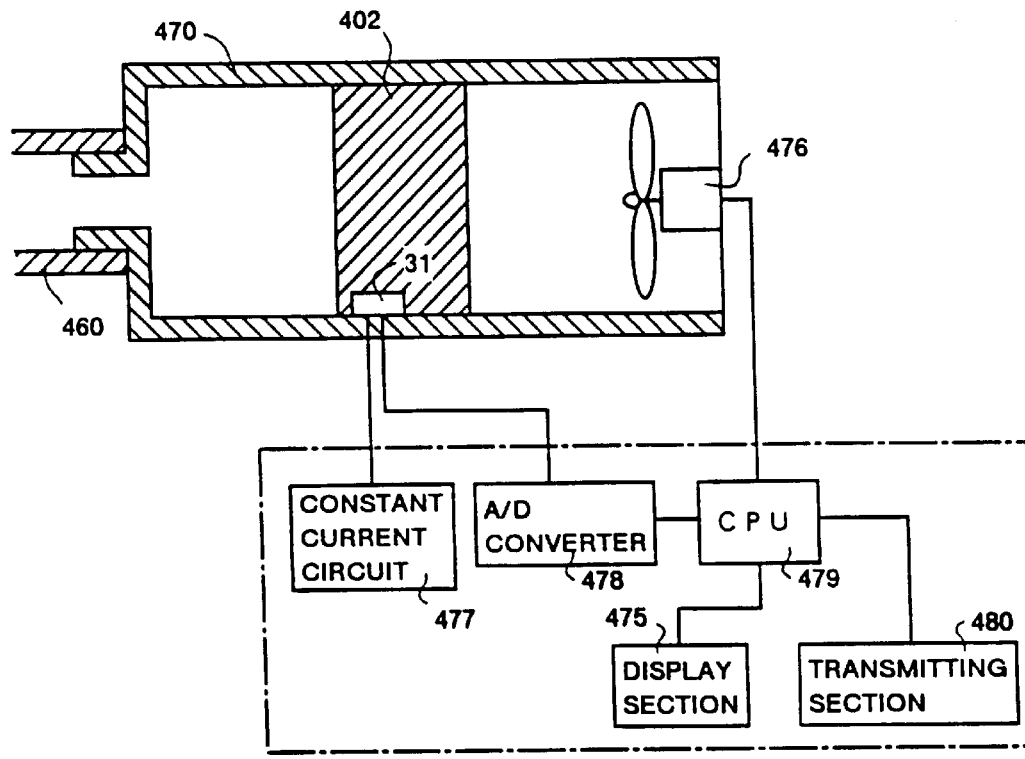
FIG. 19 is a view showing general configuration of the air line mask shown in FIG. 18.

FIG. 19 is a perspective view showing an air line mask 400 shown in FIG. 18. A filter 402 and a fan 476 for sending air are provided in the housing of the electric blower 470. Also, the semiconductor gas sensor 31 is incorporated at a position adjacent to the downstream side of the filter 402. The reason is that the passage can be detected before it actually occurs.

The electric blower 470 comprises a constant current circuit 477 for feeding a constant current to a heater in the semiconductor gas sensors 31, an A/D converter 478 for subject output from the sensor 31 to A/D converter, a CPU 479 for executing specified processing according to signals from the A/D converter 478, a transmitting section 480 for transmitting the fact that the passage has been generated to the communicating unit 415, and a display section 475 for displaying the state of the passage or the like.

Figure 20:
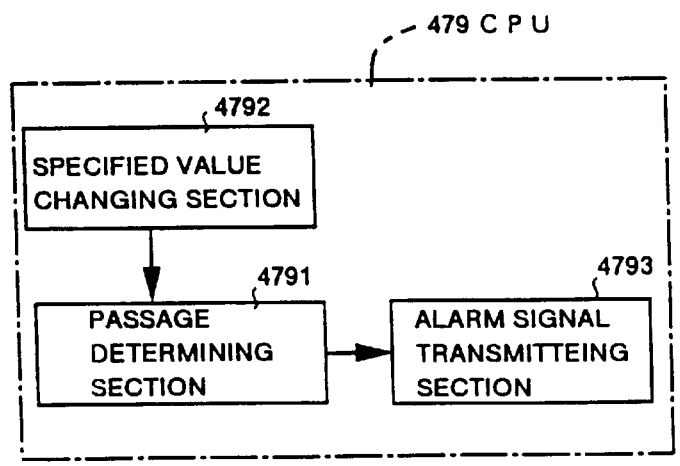
FIG. 20 is a functional block diagram showing functions of the CPU shown in FIG. 19.

FIG. 20 is a functional block diagram showing functions of the CPU 479 shown in FIG. 18. The CPU 479 comprises a passage determining section 4791 for determining that the passage has been generated in a filter 402 when a resistance value in the semiconductor gas sensors 31 exceeds a specified value described later, a specified value changing section 4792 capable of changing the specified value according to types of poisonous substances, and an alarm signal transmitting section 4793 for outputting an alarm signal to the communicating unit 415 which the user puts on when the passage determining section 4791 determines that the passage has been generated.

Figure 21:
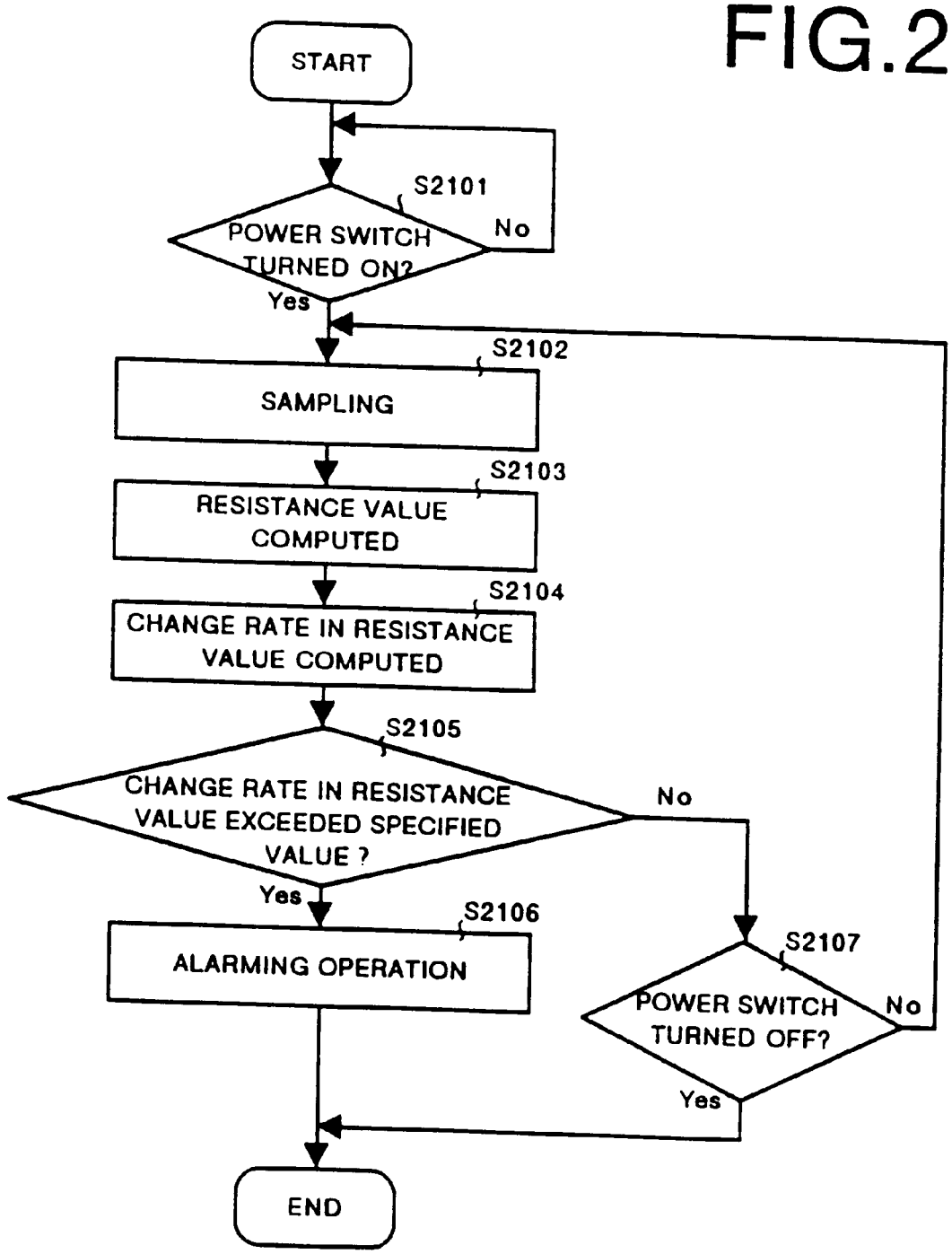
FIG. 21 is a flow chart showing a controlling process with the CPU shown in FIGS. 12A and 12B.

FIG. 21 is a flow chart showing a procedure of controlling the CPU 479 shown in FIG. 19. In step S2101, a user turns the power switch ON. Control of the CPU 479 is started simultaneously when the switch is turned ON.

In step S2102, a result of detection executed by the semiconductor gas sensor 31 is sampled. A sampling interval is around 30 seconds. In step S2103, a resistance value of the semiconductor gas sensor 31 is computed from a result of the detection. Then, in step S2104, a change rate in the resistance value is computed from the computed resistance value. If the passage is generated, the resistance value of the semiconductor gas sensor 31 is changed (Refer to FIG. 6).

In step S2105, determination is made as to whether the computed change rate in the resistance value has exceeded a specified value or not. This determination is made by the passage determining section 4791. The specified value is previously set according to the sensitivity of the semiconductor gas sensor 31 as shown in Embodiment 1. Also, it is desirable to change this specified value according to any of poisonous substances as required. This change is executed with the specified value changing section 4792. If it is determined that the change rate has exceeded the specified value, system control goes to step S2106. If it is determined that the change rate has not exceeded the specified value, system control goes to step S2107.

In step S2106, when it is determined that the passage has been generated, an operation for issuing an alarm is executed. The alarming operation is executed according to a signal from the alarm signal transmitting section 7493. For instance, the fact that the passage has been generated is displayed on the display section 475. The user is notified that the passage has been generated by means of a warning beep or an audio signal through the communicating unit 415. In addition to the means described above, vibration may be given to the user or a lamp for alarming may be lit up.

On the other hand, in step S2107, determination is made as to whether the power switch 474 is OFF or not. If it is determined that the power switch 474 is OFF, control of the CPU 479 is terminated. If it is determined that the power switch 474 is still ON, the control of the CPU 479 is continued. In this case, determination is made that the passage has not been generated because the change rate in the resistance value of the semiconductor gas sensor has not exceeded the specified value. Then the sampling of a result of detection by the semiconductor gas sensor 31 is continued until the change rate in the resistance value exceeds the specified value (steps S2102 to S2105).

Figure 22:
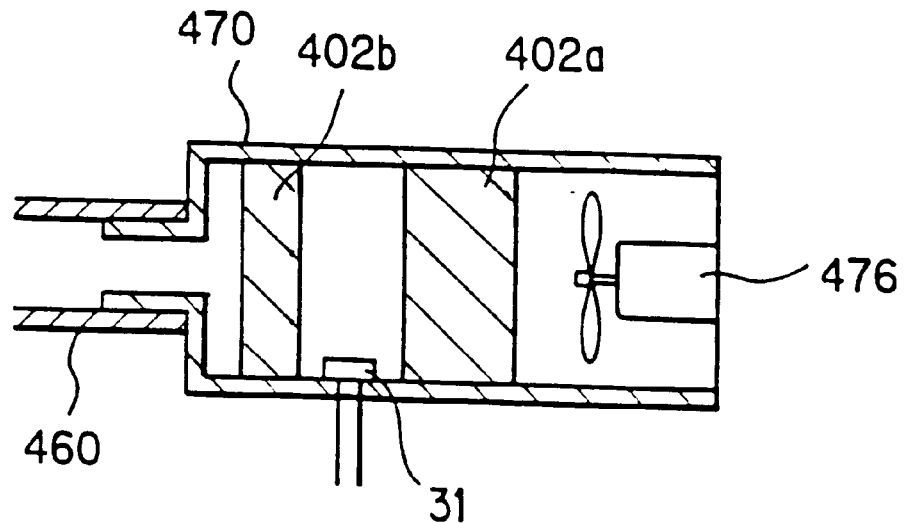
FIG. 22 is a view showing general configuration of Variant 1 of the gas mask shown in FIG. 18.

FIG. 22 is a schematic block diagram showing variant 1 of the air line mask 400 shown in FIG. 18. An upstream side filter 402a and a downstream side filter 402b are packed in the housing of the electric blower 470. A semiconductor gas sensor 31 is provided between the filter 402a and the filter 402b. A fan 476 for sending air is also provided in the housing of the electric blower 470. Other configuration of Variant 1 is the same as that in the air line mask 400.

Generation of the passage in the upstream side filter 402a is detected by the semiconductor gas sensor 31. If the generation is detected, the operation for issuing an alarm in step S2106 (FIG. 21) is executed. For instance, the fact that the passage has been generated is displayed on the display section 475. The user is notified that the passage has been generated by means of a warning beep or an audio signal through the communicating unit 415. Any of poisonous substances which passes through the upstream filter is absorbed by the downstream filter 402b. For this reason, the user will never absorb any poisonous substances which pass therethrough. Further, it takes a long period of time for the materials to pass through the filter 402b in the downstream side, so that the user may stop working during the period of time and leave the site.

Figure 23:
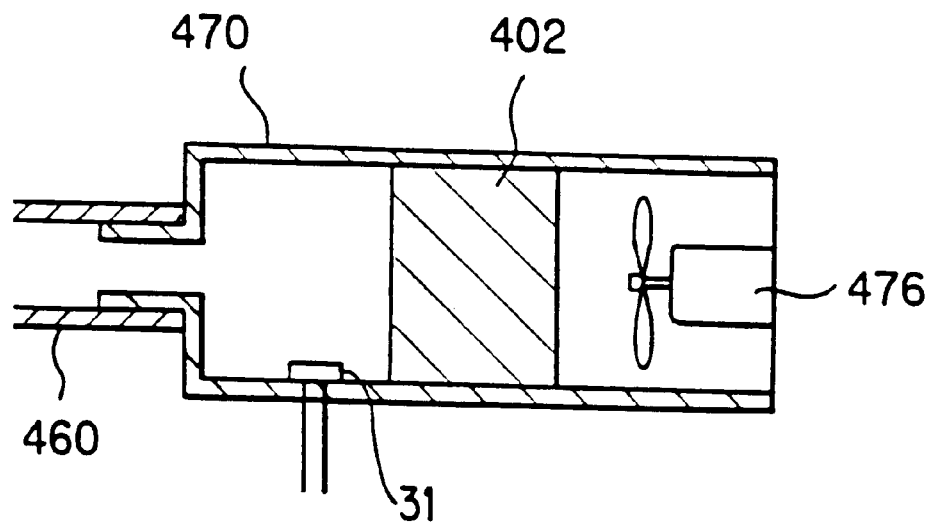
FIG. 23 is a view showing general configuration of Variant 2 of the gas mask shown in FIG. 18.
Figure 24:
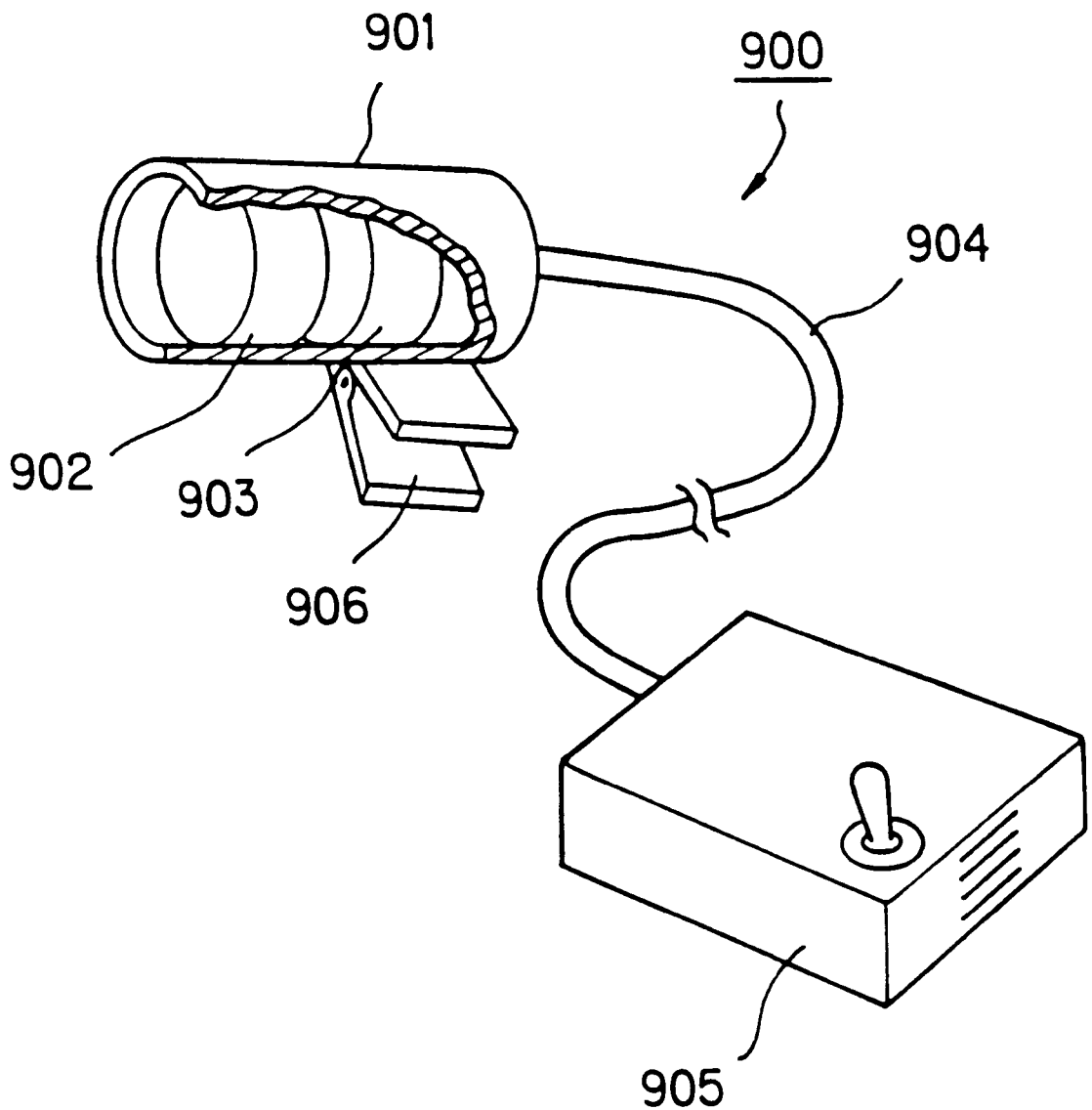
FIG. 24 is a partially broken perspective view showing a solid material collector based on the conventional technology.
Figure 25:
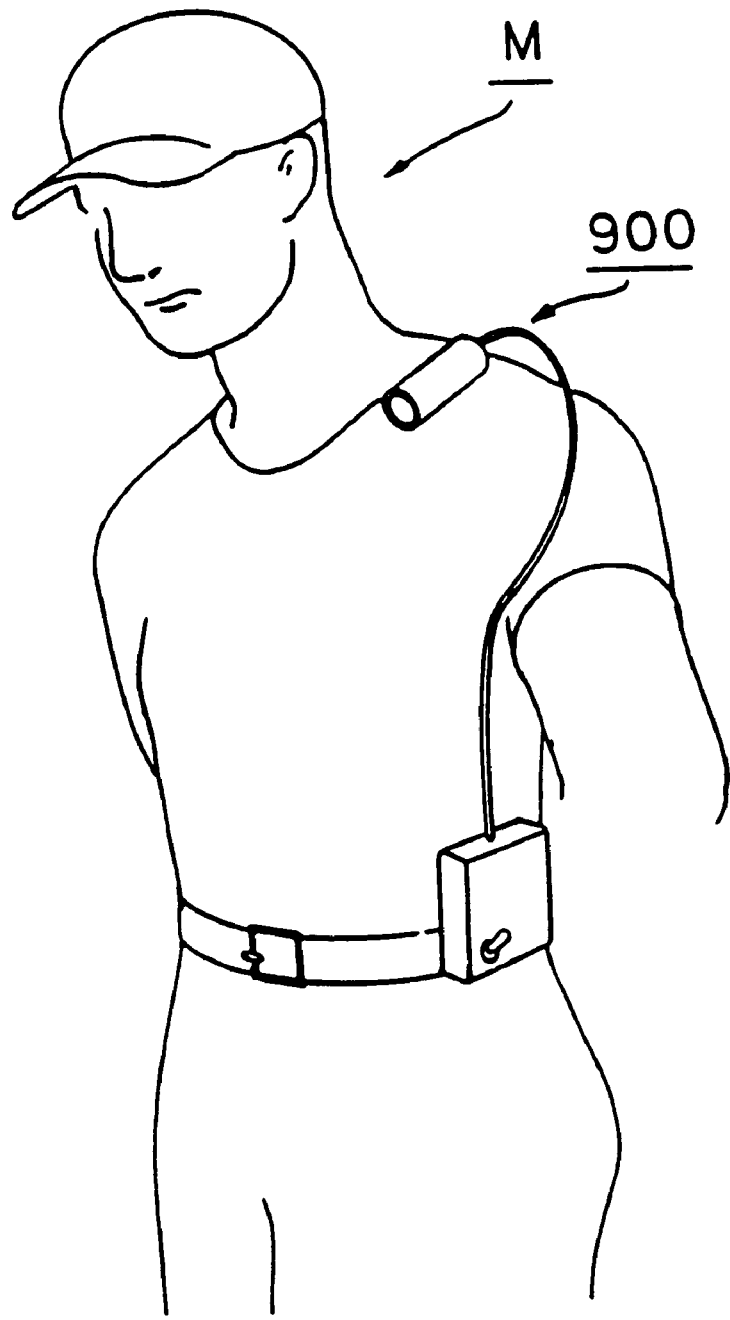
FIG. 25 is an explanatory view showing a state where the solid material collector shown in FIG. 24 is set.

FIG. 23 is a schematic block diagram showing Variant 2 of the air line mask 400 shown in FIG. 18. A filter 402 is packed in the housing of the electric blower 470. A semiconductor gas sensor 31 is provided in the downstream side of this filter 402. A fan 476 for sending air is also provided in the housing of the electric blower 470. Other configuration of Variant 2 is the same as that in the air line mask 400.

Generation of the passage in the filter 402 is detected by the semiconductor gas sensor 31. If the generation is detected, the operation for issuing an alarm in step S2106 (FIG. 21) is executed. For instance, the fact that the passage has been generated is displayed on the display section 475. The user is notified that the passage has been generated by means of a warning beep or an audio signal through the communicating unit 415. Then the user stops working and leaves site after the fact is notified.

As described above, provision of the semiconductor gas sensor 31 in the downstream side form the filter 402 makes the configuration of the air line mask simpler. Also the manufacturing is made easier, whereby a low price device can be obtained.

As explained above, the solid material collector according to the present invention can determine with by a detecting means whether passage of a material to be measured through an absorbent has actually been generated or not in the step of collecting the material at real time. For this reason, a result of measurement is prevented from becoming unreliable. Also, it is possible to prevent measurement from being continued in a state where the passage has been generated, so that measurement can be executed accurately. Size of the solid material collector can be reduced because the detecting means is small in size and there is no need to increase an quantity of adsorbent used therein.

The solid material collector according to the present invention comprises a detecting means incorporated at a position adjacent to an edge in the downstream side of a collecting means; so that it can detect the material to be measured right before the passage is actually generated. Therefore, the passage can be prevented before it actually occurs, and measurement can be executed more accurately.

The solid material collector according to the present invention uses activated carbon, silica gel, porous polymer beads, Florysil, or filter paper with a specific reagent reactive to a material to be measured impregnated therein, as the collecting means. Therefore, the operation for collecting can be executed appropriately.

The solid material collector according to the present invention uses a semiconductor gas sensor as the detecting means. The semiconductor gas sensor can detect almost all types of organic solvent vapor non-selectively, and it has high sensitivity . Thus, it can detect the passage precisely. The semiconductor gas sensor itself is relatively less expensive, whereby the solid material collector can be provided at low cost.

The solid material collector according to the present invention notifies a user, when said detecting means detects the material to be measured, of the fact. Therefore, by taking necessary measures such as stopping the operation for collecting, measurement can be executed efficiently and accurately and a reliable result can be obtained.

The solid material collector according to the present invention automatically stops the operation of the sucking means when an output from said detecting means exceeds a specified value. Thus, effects of the passage can be suppressed to a minimum level, and measurement can be executed accurately. Also, a reliable result of measurement can be obtained.

In the solid material collector according to the present invention, it is possible to change the specified value according to a material to be measured. For this reason, the solid material collector can appropriately respond to various types of materials to be measured, and execute the operation for measurement accurately.

The solid material collector according to the present invention records a point of time when operation of a sucking means is started, and measures actual time when operation for collecting is actually executed. Measurement can be executed without being bothered by considerations to a period of time where the passage is actually generated.

The solid material collector according to present invention comprises a plurality of said detecting means and selects other detecting means when dispersion is generated in output from one detecting means. For this reason, reliability of the output from the detecting means becomes higher, and measurement can be executed accurately.

A density measuring method according to the present invention stops the operation for collecting when the passage is detected and measures a density of a material to be measured in a state where there is no effect of the passage. For this reason, accurate measurement can be executed.

The density measuring method according to the present invention detects the passage right before it is generated, and executes the operation for measuring in a state where the passage has not been generated. For this reason, the operation for collecting can be executed most effectively and further measurement can be executed more accurately.

The gas mask according to the present invention detects the passage generated in the gas mask by a detecting means incorporated at a position adjacent to an edge section in the downstream side of a collecting means. For this reason, the passage can be detected before it is actually generated, which insures higher safety of the gas mask.

The gas mask according to the present invention comprises two layers of collecting means, detects poisonous substance having passed through the collecting means in the upstream side, and collects the poisonous substance with the collecting means in the downstream side. Therefore, even though the passage is generated in the collecting means in the upstream side, a user will not receive any damage with the poisonous substance. This insures higher safety of the gas mask.

The gas mask according to the present invention provides the detecting means in the downstream side from the collecting means and detects the poisonous substance coming into a mask body. This configuration is simpler than that of the gas mask described above, which makes the cost less expensive. Also safety of the gas mask is insured.

In the gas mask according to the present invention, the collecting means is activated carbon, silica gel, porous polymer beads, Florysil, or filter paper with a specific reagent reactive to the material to be measured impregnated therein. Therefore, an operation for collecting poisonous materials can be executed appropriately.

The gas mask according to the present invention uses a semiconductor gas sensor as the detecting means. The semiconductor gas sensor can detect almost all types of organic solvent vapor non-selectively, and it has high sensitivity. Therefore, it can detect passage of the poisonous substance accurately, which insures higher safety of the gas mask.

The gas mask according to the present invention comprises an alarming means for notifying a user, when said detecting means detects any poisonous substance, of the fact, and instructs the user to take necessary measures. For this reason, higher safety of the gas mask is insured.

The gas mask according to the present invention comprises a plurality of said detecting means and selects other detecting means when dispersion is generated in output from one detecting means. With this configuration, reliability of the output from the detecting means is obtained, and higher safety of the gas mask is insured.

The gas mask according to the present invention comprises a notifying means for notifying a manager or a person other than the user, when said detecting means detects any poisonous substance, of the fact. Therefore, measures for safety and rescue can be taken.

In an air line mask according to the present invention, the detecting means for detecting a poisonous substance is incorporated at a position adjacent to an edge section in the downstream side of the collecting means, which is provided between the blasting means and said mask body. For this reason, it can detect the passage right before the passage is actually generated, so that higher safety of the air line mask is insured.

The air line mask according to the present invention comprises two layers of collecting means, and also a detecting means for detecting the poisonous substance between the collecting means. The detecting means detects poisonous substance having passed through the collecting means in the upstream side. And the poisonous substance having passed through the collecting means is collected by the collecting means in the downstream side. For this reason, higher safety of the air line mask is insured.

The air line mask according to the present invention comprises a detecting means for detecting the poisonous substance provided in the downstream side from the collecting means. For this reason, higher safety of the air line mask is insured. The configuration of this air line mask is simpler than that of the air line mask described above, which makes its cost less expensive.

The air line mask according to the present invention notifies the user, when the detecting means detects any poisonous substance, of the fact. For this reason, the user is notified of generation of the passage even if the passage occurs at a position away from the user. This insures higher safety of the air line mask.

Although the invention has been described with respect to a specific embodiment for a complete and clear disclosure, the appended claims are not to be thus limited but are to be construed as embodying all modifications and alternative constructions that may occur to one skilled in the art which fairly fall within the basic teaching herein set forth.

What is claimed is:

1. A density measuring method for measuring a density of a material collected in a working environment by a collecting unit configured to collect the material to be measured, said method comprising:

receiving and collecting the material from the working environment in the collecting unit at an upstream side of the collecting unit;

providing a detector configured to detect the material at a downstream side of the collecting unit, said downstream side being a side opposite to the upstream side;

detecting passage of the material through said collecting unit by said detector;

stopping the step of receiving and collecting the material when said passage is detected; and measuring the density of said material by quantifying the material being collected in said collecting unit until the step of stopping the receiving and collecting of the material.

2. A density measuring method for measuring a density of a material collected in a working environment, said method comprising:

collecting the material in a collecting unit;

detecting the passage of the material through the collecting unit at a position adjacent to a downstream side of said collecting unit, said downstream side being opposite to a side of the collecting unit initially receiving the material being collected;

stopping the step of collecting the material when said material is detected in said detecting step; and measuring a density of the material by quantifying the material collected by said collecting unit until the step of stopping the collecting of the material occurs.

* * * * *